US012281314B2

(12) United States Patent
Coller et al.

(10) Patent No.: US 12,281,314 B2
(45) Date of Patent: Apr. 22, 2025

(54) METHODS AND COMPOSITIONS FOR INCREASING PROTEIN EXPRESSION AND/OR TREATING A HAPLOINSUFFICIENCY DISORDER

(71) Applicants: CASE WESTERN RESERVE UNIVERSITY, Cleveland, OH (US); WHITEHEAD INSTITUTE FOR BIOMEDICAL RESEARCH, Cambridge, MA (US)

(72) Inventors: Jeffery M. Coller, Novelty, OH (US); Thomas Sweet, Cleveland, OH (US); Harvey Lodish, Cambridge, MA (US)

(73) Assignees: CASE WESTERN RESERVE UNIVERSITY, Cleveland, OH (US); WHITEHEAD INSTITUTE FOR BIOMEDICAL RESEARCH, Cambridge, MA (US)

( * ) Notice: Subject to any disclaimer, the term of this patent is extended or adjusted under 35 U.S.C. 154(b) by 973 days.

(21) Appl. No.: 17/280,369

(22) PCT Filed: Sep. 26, 2019

(86) PCT No.: PCT/US2019/053268
§ 371 (c)(1),
(2) Date: Mar. 26, 2021

(87) PCT Pub. No.: WO2020/069199
PCT Pub. Date: Apr. 2, 2020

(65) Prior Publication Data
US 2022/0073933 A1 Mar. 10, 2022

Related U.S. Application Data

(60) Provisional application No. 62/736,847, filed on Sep. 26, 2018.

(51) Int. Cl.
| | | |
|---|---|---|
| C12N 15/67 | (2006.01) | |
| A61K 31/7088 | (2006.01) | |
| A61K 45/06 | (2006.01) | |
| A61K 48/00 | (2006.01) | |
| A61P 43/00 | (2006.01) | |
| C12N 15/11 | (2006.01) | |
| C12N 15/86 | (2006.01) | |

(52) U.S. Cl.
CPC .......... *C12N 15/67* (2013.01); *A61K 31/7088* (2013.01); *A61K 45/06* (2013.01); *A61K 48/0066* (2013.01); *A61P 43/00* (2018.01); *C12N 15/11* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | |
|---|---|---|
| 7,745,391 B2 | 6/2010 | Mintz et al. |
| 9,676,810 B2 | 6/2017 | Anderson et al. |
| 10,597,721 B2 | 3/2020 | Hatchwell et al. |
| 2013/0129668 A1 | 5/2013 | Firestein et al. |

FOREIGN PATENT DOCUMENTS

| | | |
|---|---|---|
| JP | 2002-525048 A | 8/2002 |
| WO | 2012/006551 A1 | 1/2012 |
| WO | 2015/048989 A1 | 4/2015 |
| WO | 2017/066482 A1 | 4/2017 |
| WO | 2017/193051 A1 | 11/2017 |
| WO | 2017/201091 A1 | 11/2017 |
| WO | 2018/104385 A1 | 6/2018 |
| WO | 2020/243560 A1 | 12/2020 |

OTHER PUBLICATIONS

Koukuntla, Ramesh. "Suppressor tRNA mediated gene therapy." (2009). (Year: 2009).*
Tan EH, Razak SA, Abdullah JM, Mohamed Yusoff AA. De-novo mutations and genetic variation in the SCN1A gene in Malaysian patients with generalized epilepsy with febrile seizures plus (GEFS+). Epilepsy Res. Dec. 2012;102(3):210-5. doi: 10.1016/j.eplepsyres.2012.08.004. Epub Sep. 1, 2012. PMID: 22944210. (Year: 2012).*
Bechi, Guilia, "Pure haploinsufficiency for Dravet syndrome Nav1.1 (SCN / A) sodium channel truncating mutations", Epilepsia, 53(1):87-100, 2012.
Hsiao, J., et al., "Upregulation of Haploinsufficient Gene Expression in the Brain by Targeting a Long Non-coding RNA Improves Seizure Phenotype in a Model of Dravet Syndrome", EBioMedicine 9 (2016) 257-277.
European Application No. 19866182.9, Extended Search Report dated May 19, 2023.
Muallif Siti Aisyah, et al., "Engineering and Validation of a Vector for Concomitant Expression of Rare Transfer RNA (tRNA) and HIV-1 nef Genes in *Escherichia coli*", PLOS One, vol. 10, No. 7, Jul. 6, 2015.
Kirchner, Sebastian, et al., "Alteration of Protein Function by a Silent Polymorphism linked to tRNA abundance", PLOS Biology, vol. 15, No. 5, May 16, 2017.
Chinese Application No. 20198007435.7, Office Action dated Aug. 19, 2023.
Japanese Application No. 2021-517022, Office Action dated Aug. 29, 2023.
PLOS Biology, 2017, 15(5): e2000779, pp. 1 to 29.
Neurogenetics, 2006, 7(1), pp. 59 to 66.
Hum. Mutat., 2004, 24(6), pp. 534 to 535.

(Continued)

*Primary Examiner* — Fereydoun G Sajjadi
*Assistant Examiner* — Qinhua Gu
(74) *Attorney, Agent, or Firm* — Tarolli, Sundheim, Covell & Tummino LLP

(57) ABSTRACT

A tRNA that hybridizes to a non-optimal codon can be used to increase expression in a mammalian cell of a gene product encoded by a gene containing the non-optimal codon or to treat a haploinsufficiency disorder in a subject having a haploinsufficient gene containing the non-optimal codon.

10 Claims, 3 Drawing Sheets

Specification includes a Sequence Listing.

(56) References Cited

OTHER PUBLICATIONS

Eurasian Application No. 202190736, Office Action dated Nov. 21, 2023.
European Application No. 19866182.9, Office Action dated Apr. 19, 2024.
Korean Application No. 10-2021-7012452, Office Action dated May 9, 2024.
Japanese Application No. 2021-517022, Office Action dated May 28, 2024.
Australian Application No. 2019350871, Examination Report dated Feb. 18, 2025.

* cited by examiner

| position | residues | ratios | position | residues | ratios |
|---|---|---|---|---|---|
| 0 | Gm/G | 1/4 | 35 | Ψ/U | 7/50 |
| 1 | Ψ/U | 3/14 | 36 | Ψ/xU/U | 2/3/50 |
| 4 | Am/A | 2/28 | 37 | $m^1$I/$ms^2t^6A$/$t^6A$/ | 6/2/22/ |
| 4 | Um/U | 5/45 | 37 | $m^6t^6A$/$i^6A$/xA/A | 2/48/4/45 |
| 4 | Cm/C | 4/51 | 37 | $m^1G$/o2yW/xG/ | 33/85/2/ |
| 4 | Gm/G | 2/41 |  | xW/G | 7/1 |
| 6 | $m^2G$/G | 20/38 | 38 | Ψ/U | 17/1 |
| 7 | $m^2G$/G | 1/59 | 38 | $m^5C$/xC/C | 10/1/26 |
| 9 | $m^1A$/A | 1/59 | 39 | $m^1Ψ$/Ψ/mv/ | 2/8/ |
| 9 | $m^1G$/xG/G | 56/1/43 |  | Um/xΨ/U | 1/1/79/2 |
| 10 | $m^2G$/G | 103/70 | 39 | Gm/G | 4/32 |
| 12 | $ac^4C$/C | 32/21 | 40 | Ψ/U | 6/1 |
| 13 | Ψ/U | 47/8 | 40 | $m^5C$/C | 2/139 |
| 13 | Cm/C | 1/83 | 44 | Um/xU/U | 20/2/18 |
| 14 | $m^1A$/xA/A | 9/1/165 | e11 | Ψ/U | 2/4 |
| 16 | D/U | 123/25 | e12 | Ψ/U | 5/11 |
| 17 | D/U | 39/9 | e14 | Ψ/U | 2/8 |
| 18 | Gm/G | 40/139 | e2 | $m^5C$/C | 7/7 |
| 20 | $acp^3U$/D/U | 4/118/11 | 46 | $m^7G$/G | 86/39 |
| 20a | $acp^3U$/D/Ψ/xU/U | 6/64/2/2/2 | 47 | D/xU/U | 83/1/16 |
| 20b | D/Ψ/U | 6/6/2 | 48 | D/U | 1/28 |
| 25 | Ψ/U | 1/28 | 48 | $m^5C$/xC/C | 95/1/46 |
| 26 | Ψ/U | 1/34 | 49 | xA/A | 1/19 |
| 26 | $m^{2,2}G$/$m^2G$/xG/G | 90/16/3/8 | 49 | $m^5C$/xC/C | 64/1/13 |
| 27 | Ψ/U | 70/10 | 50 | Ψ/U | 4/45 |
| 27 | $m^{2,2}G$/G | 2/14 | 50 | $m^5C$/C | 15/71 |
| 28 | Ψ/U | 37/38 | 54 | $m^5U$/mv/$m^5$Ψ/U | 16/1/1/1/17 |
| 30 | Ψ/U | 1/4 | 55 | Ψ/U | 166/12 |
| 31 | Ψ/U | 4/2 | 58 | $m^1A$/xA/A | 151/1/28 |
| 32 | Ψm/Um/$m^5$Ψ/U | 2/6/24/8 | 64 | Ar(p)A | 2/43 |
| 32 | Cm/$m^5C$/xC/C | 40/16/2/60 | 64 | Gr(p)/xG/G | 1/1/87 |
| 34 | I/A | 32/3 | 65 | Ψ/U | 1/32 |
| 34 | $s^2U$/Um/mchm$^5U$/ | 1/3/1/ | 67 | Ψ/U | 2/83 |
|  | mcm$^5U$/cmnm$^5$Um/ | 3/1/ | 67 | $m^2G$/G | 2/64 |
|  | mcm$^5$Ψ/U/mcm$^5U$/ | 7/4/ | 68 | Ψ/U | 1/37 |
|  | Ψ/xU/U | 1/11/6 | 72 | Ψ/U | 1/16 |
| 34 | Cm/$l^5$Cm/$m^5C$/xC/C | 8/1/1/2/44 | 72 | $m^5C$/C | 5/132 |
| 34 | QtRNA/manQtRNA/galQtRNA/Gm/G | 5/4/ 3/17/20 |  |  |  |

Fig. 2B

METHODS AND COMPOSITIONS FOR INCREASING PROTEIN EXPRESSION AND/OR TREATING A HAPLOINSUFFICIENCY DISORDER

RELATED APPLICATION

This application claims priority from U.S. Provisional Application No. 62/736,847, filed Sep. 26, 2018, the subject matter of which is incorporated herein by reference in its entirety.

SEQUENCE LISTING

The instant application contains a Sequence Listing which has been submitted electronically in TXT format and is hereby incorporated by reference in its entirety. Said .TXT copy, created on Sep. 23, 2019, is named CWR027998WOORDSEQUENCELISTING.TXT and is 4,577 bytes in size.

FIELD OF THE INVENTION

This disclosure relates generally to methods and compositions for increasing expression of a gene product encoded by a gene containing a non-optimal codon and/or treating a haploinsufficiency disorder in a subject.

BACKGROUND

Haploinsufficiency occurs when one gene allele is inactivated and the amount of gene product expressed from the remaining active allele is insufficient for proper gene function. A number of disorders are associated with, or are caused by haploinsufficiency.

An example of a haploinsufficiency disorder is Dravet Syndrome. Dravet Syndrome is a rare and catastrophic form of intractable epilepsy that begins in infancy. Initially, patients experience prolonged seizures. In their second year, additional types of seizure begin to occur, which typically coincide with a developmental decline, possibly due to repeated cerebral hypoxia. This leads to poor development of language and motor skills. Mutations in SCN1A (encoding the voltage-gated sodium channel α subunit), SCN1B (encoding the voltage-gated sodium channel β1 subunit), SCN2A, SCN3A, SCN9A, GABRG2 (encoding the γ-aminobutyric acid receptor γ2 subunit), GABRD (encoding the γ-aminobutyric acid receptor Δ subunit) and/or PCDH19 genes have been linked to Dravet Syndrome.

For example, Dravet syndrome may be caused by a mutation in the SCN1A gene resulting in inactivation of one SCN1A gene allele and a lack of or reduced amount of functional SCN1A gene product. The SCN1A gene normally codes for the neuronal voltage-gated sodium channel α subunit, Na(V)1.1. In mouse models, loss-of-function mutations in SCN1A have been observed to result in a decrease in sodium currents and impaired excitability of GABAergic interneurons of the hippocampus.

Accordingly, there is a need in the art for improved compositions and methods for increasing protein expression and treating diseases mediated by haploinsufficiency, including Dravet syndrome.

SUMMARY

This disclosure relates generally to methods and compositions for increasing expression of a gene product encoded by a gene containing a non-optimal codon and/or treating a haploinsufficiency disorder in a subject. The presence of a non-optimal codon in a gene of interest results in a destabilization of mRNA transcribed from the gene, which can impact the production of functional protein encoded by the gene. Under such situations, destabilization of the mRNA transcript can occur when, for example, the abundance of a specific aminoacylated tRNA molecule that hybridizes to the non-optimal codon is lower than other, different tRNAs available in a cell that are aminoacylated with the same amino acid. Surprisingly, it has been discovered that increasing the abundance of such a tRNA in a cell relative to the other, naturally more abundant tRNAs can promote the expression and/or amount of functional protein produced by the cell. Expression of a gene product, e.g., a protein, can be increased and/or selectively increased (i.e., the expression of the gene product can be increased more than another gene product or more than any other gene product) by the introduction into the cell of a minimal number (e.g., 1, 2, or 3) of tRNAs that decode non-optimal codons in the gene.

Similarly, for a subject having a gene containing a non-optimal codon, administration to the subject of an effective amount of a tRNA that decodes the non-optimal codon can increase expression of a gene product from the gene in the subject. Accordingly, administration of the tRNA to the subject can treat a disease in the subject that is mediated by insufficient expression of the gene product, for example, a haploinsufficiency disorder. In addition, features of the methods and compositions described herein make them desirable for use in treatment of disorders, e.g., haploinsufficiency disorders, in human subjects. For example, tRNAs are relatively small in size and can be produced recombinantly, and the methods and compositions described herein can treat a haploinsufficiency disorder regardless of the mutation or mechanism by which an allele was inactivated.

Accordingly, in one aspect, this disclosure provides a method of increasing expression in a mammalian cell of a gene product encoded by a gene containing a first non-optimal codon. The method includes introducing into the cell an effective amount of a first exogenous tRNA that (i) comprises an anticodon that hybridizes to the first non-optimal codon, and (ii) is capable of being aminoacylated with an amino acid, wherein introduction of the first exogenous tRNA into the cell increases the expression of the gene product relative to a similar cell lacking the first exogenous tRNA.

In certain embodiments, the gene contains a second non-optimal codon, and the method further comprises introducing into the cell an effective amount of a second exogenous tRNA that (i) comprises an anticodon that hybridizes to the second non-optimal codon, and (ii) is capable of being aminoacylated with an amino acid, wherein introduction of the second exogenous tRNA into the cell increases the expression of the gene product relative to a similar cell lacking the second exogenous tRNA. In certain embodiments, the gene contains a third non-optimal codon, and the method further comprises introducing into the cell an effective amount of a third exogenous tRNA that (i) comprises an anticodon that hybridizes to the third non-optimal codon, and (ii) is capable of being aminoacylated with an amino acid, wherein introduction of the third exogenous tRNA into the cell increases the expression of the gene product relative to a similar cell lacking the third exogenous tRNA.

In another aspect, this disclosure provides a method of increasing expression in a mammalian cell of a gene product encoded by a gene containing a first non-optimal codon. The method includes introducing into the cell an effective amount of a first expression vector capable of expressing a first exogenous tRNA that (i) comprises an anticodon that hybridizes to the first non-optimal codon, and (ii) is capable of being aminoacylated with an amino acid, wherein expression of the first exogenous tRNA in the cell increases the expression of the gene product relative to a similar cell lacking the first exogenous tRNA.

In certain embodiments, the gene contains a second non-optimal codon, and the method further comprises introducing into the cell an effective amount of a second expression vector capable of expressing a second exogenous tRNA that (i) comprises an anticodon that hybridizes to the second non-optimal codon, and (ii) is capable of being aminoacylated with an amino acid, wherein expression of the second exogenous tRNA in the cell increases the expression of the gene product relative to a similar cell lacking the second exogenous tRNA. In certain embodiments, the gene contains a third non-optimal codon, and the method further comprises introducing into the cell an effective amount of a third expression vector capable of expressing a third exogenous tRNA that (i) comprises an anticodon that hybridizes to the third non-optimal codon, and (ii) is capable of being aminoacylated with an amino acid, wherein expression of the third exogenous tRNA in the cell increases the expression of the gene product relative to a similar cell lacking the third exogenous tRNA.

In certain embodiments, the first, second, and/or third expression vector are the same. In certain embodiments, the first, second, and/or third expression vector is a viral vector, e.g., an adeno-associated virus (AAV) vector.

In certain embodiments of any of the foregoing methods of increasing expression, the cell is a human cell. In certain embodiments, the cell is a central nervous system cell, e.g., a neuron.

In certain embodiments, the gene is selected from AGGF1, ARHGAP31, BMPR2, CHD7, COL2A1, COL3A1, CTLA4, CTNNB1, DLL4, EHMT1, ELN, ENG, FAS, FBN1, FOXG1, GATA3, GLI3, GRN, IRF6, JAG1, KCNQ4, LMX1B, MBD5, MED13L, MITF, MNX1, MYCN, NFIA, NFIX, NOTCH1, NSD1, PAX3, PHIP, PRKAR1A, RAI1, RBPJ, RPS14, RUNX2, SALL4, SCN1A, SETBP1, SHANK3, SHH, SHOX, SLC2A1/GLUT1, SOX10, SYNGAP1, TBX1, TBX3, TBX5, TCF4, TCOF1, TGIF1, TNXB, TRPS1, WT1, and ZIC2. In certain embodiments, the gene is SCN1A.

In another aspect, this disclosure provides a method of treating a haploinsufficiency disorder in a subject in need thereof wherein the subject has a haploinsufficient gene containing a first non-optimal codon. The method includes administering to the subject an effective amount of a first tRNA that (i) comprises an anticodon that hybridizes to the first non-optimal codon, and (ii) is capable of being aminoacylated with an amino acid, thereby to treat the haploinsufficiency disorder in the subject.

In certain embodiments, the haploinsufficient gene contains a second non-optimal codon, and the method further comprises administering to the subject an effective amount of a second tRNA that (i) comprises an anticodon that hybridizes to the second non-optimal codon, and (ii) is capable of being aminoacylated with an amino acid. In certain embodiments, the haploinsufficient gene contains a third non-optimal codon, and the method further comprises administering to the subject an effective amount of a third tRNA that (i) comprises an anticodon that hybridizes to the third non-optimal codon, and (ii) is capable of being aminoacylated with an amino acid.

In another aspect, this disclosure provides a method of treating a haploinsufficiency disorder in a subject in need thereof wherein the subject has a haploinsufficient gene containing a first non-optimal codon. The method includes administering to the subject an effective amount of a first expression vector capable of expressing a first tRNA that (i) comprises an anticodon that hybridizes to the first non-optimal codon, and (ii) is capable of being aminoacylated with an amino acid, thereby to treat the haploinsufficiency disorder in the subject.

In certain embodiments, the haploinsufficient gene contains a second non-optimal codon, and the method further comprises administering to the subject an effective amount of a second expression vector capable of expressing a second tRNA that (i) comprises an anticodon that hybridizes to the second non-optimal codon, and (ii) is capable of being aminoacylated with an amino acid. In certain embodiments, the haploinsufficient gene contains a third non-optimal codon, and the method further comprises administering to the subject an effective amount of a third expression vector capable of expressing a third tRNA that (i) comprises an anticodon that hybridizes to the third non-optimal codon, and (ii) is capable of being aminoacylated with an amino acid.

In certain embodiments, the first, second, and/or third expression vector are the same. In certain embodiments, the first, second, and/or third expression vector is a viral vector, e.g., an adeno-associated virus (AAV) vector.

In certain embodiments of any of the foregoing methods of treatment, the subject is a human.

In certain embodiments, the haploinsufficiency disorder is selected from 5q-syndrome, Adams-Oliver syndrome 1, Adams-Oliver syndrome 3, Adams-Oliver syndrome 5, Adams-Oliver syndrome 6, Alagille syndrome 1, Autoimmune lymphoproliferative syndrome type IA, Autoimmune lymphoproliferative syndrome type V, Autosomal dominant deafness-2A, Brain malformations with or without urinary tract defects (BRMUTD), Carney complex type 1, CHARGE syndrome, Cleidocranial dysplasia, Currarino syndrome, Denys-Drash syndrome/Frasier syndrome, Developmental delay, intellectual disability, obesity, and dysmorphic features (DIDOD), DiGeorge syndrome (TBX1-associated), Dravet syndrome, Duane-radial ray syndrome, Ehlers-Danlos syndrome (classic-like), Ehlers-Danlos syndrome (vascular type), Feingold syndrome 1, Frontotemporal lobar degeneration with TDP43 inclusions (FTLD-TDP), GRN-related, GLUT1 deficiency syndrome, Greig cephalopolysyndactyly syndrome, Hereditary hemorrhagic telangiectasia type 1, Holoprosencephaly 3, Holoprosencephaly 4, Holoprosencephaly 5, Holt-Oram syndrome, Hypoparathyroidism, sensorineural deafness, and renal disease (HDR), Kleefstra syndrome 1, Klippel-Trenaunay syndrome (AAGF-related), Leri-Weill dyschondrosteosis, Marfan syndrome, Mental retardation and distinctive facial features with or without cardiac defects (MRFACD), Mental retardation, autosomal dominant 1, Mental retardation, autosomal dominant 19, Mental retardation, autosomal dominant 29, Nail-patella syndrome (NPS), Phelan-McDermid syndrome, Pitt-Hopkins syndrome, Primary pulmonary hypertension 1, Rett syndrome (congenital variant), Smith-Magenis syndrome (RAI1-associated), Sotos syndrome 1, Sotos syndrome 2, Stickler syndrome type I, Supravalvular aortic stenosis, SYNGAP1-related intellectual disability, Treacher Collins syndrome, Trichorhinophalangeal syndrome type I, Ulnar-mammary syndrome, van der Woude syndrome 1, Waardenburg syndrome type 1, Waardenburg syndrome type 2A, and Waardenburg syndrome type 4C. In certain embodiments, the haploinsufficiency disorder is Dravet syndrome.

In certain embodiments, the haploinsufficient gene is selected from AGGF1, ARHGAP31, BMPR2, CHD7, COL2A1, COL3A1, CTLA4, CTNNB1, DLL4, EHMT1, ELN, ENG, FAS, FBN1, FOXG1, GATA3, GLI3, GRN, IRF6, JAG1, KCNQ4, LMX1B, MBD5, MED13L, MITF, MNX1, MYCN, NFIA, NFIX, NOTCH1, NSD1, PAX3, PHIP, PRKAR1A, RAI1, RBPJ, RPS14, RUNX2, SALL4, SCN1A, SETBP1, SHANK3, SHH, SHOX, SLC2A1/ GLUT1, SOX10, SYNGAP1, TBX1, TBX3, TBX5, TCF4, TCOF1, TGIF1, TNXB, TRPS1, WT1, and ZIC2. In certain embodiments, the haploinsufficient gene is SCN1A.

In certain embodiments, the haploinsufficiency disorder is a disorder listed in TABLE 1 or TABLE 2 below, and the haploinsufficient gene is a gene listed in the corresponding row of TABLE 1 or TABLE 2 below.

In certain embodiments, the method further comprises administering DIACOMIT® (stiripentol), EPIODOLEX® (cannabidiol), a ketogenic diet, ONFI® (clobazam), TOPAMAX® (topiramate), or valproic acid to the subject.

In certain embodiments of any of the foregoing methods, the gene is a gene listed in TABLE 1 or TABLE 2 below, and the first, second, and/or third non-optimal codon is a codon listed in the corresponding row of TABLE 1 or TABLE 2 below. In certain embodiments, the haploinsufficiency disorder is a disorder listed in TABLE 1 or TABLE 2 below, and the first, second, and/or third non-optimal codon is a codon listed in the corresponding row of TABLE 1 or TABLE 2 below.

In certain embodiments of any of the foregoing methods, the first, second, and/or third non-optimal codon is selected from ATA, GTA, and AGA.

In certain embodiments of any of the foregoing methods, the first, second, and/or third tRNA is selected from a tRNA comprising a nucleotide sequence of SEQ ID NO: 1, SEQ ID NO: 2 and SEQ ID NO: 3. In certain embodiments, the first, second, and/or third expression vector comprises a nucleotide sequence selected from SEQ ID NO: 4, SEQ ID NO: 5, SEQ ID NO: 6, SEQ ID NO: 7, SEQ ID NO: 8, and SEQ ID NO: 9.

In another aspect, this disclosure provides an expression vector comprising a nucleic acid encoding a first, second, and/or third tRNA that (i) comprises an anticodon that hybridizes to the third non-optimal codon, and (ii) is capable of being aminoacylated with an amino acid. In certain embodiments, the expression vector comprises the nucleotide sequence of SEQ ID NO: 1, SEQ ID NO: 2, and/or SEQ ID NO: 3. In certain embodiments, the expression vector comprises the nucleotide sequence of SEQ ID NO: 4, SEQ ID NO: 5, SEQ ID NO: 6, SEQ ID NO: 7, SEQ ID NO: 8, and/or SEQ ID NO: 9. In certain embodiments, the expression vector is a viral vector, e.g., a DNA virus vector, e.g., an adeno-associated virus (AAV) vector. In another aspect, this disclosure provides a pharmaceutical composition comprising any of the foregoing expression vectors and a pharmaceutically acceptable excipient.

These and other aspects and features of the invention are described in the following detailed description and claims.

DESCRIPTION OF THE DRAWINGS

The invention can be more completely understood with reference to the following drawings.

FIG. 2B is a table showing the modification profile for tRNA sequences from the cytosol of certain eukaryotic organisms. The ratios in the table indicate the frequency of occurrence of listed nucleotide at the numbered position shown in FIG. 2A. The abbreviations for the modified residues are defined in Motorin et al. (2005) "Transfer RNA Modification," ENCYCLOPEDIA OF LIFE SCIENCES, John Wily & Sons, Inc.

DETAILED DESCRIPTION

Figure 1:
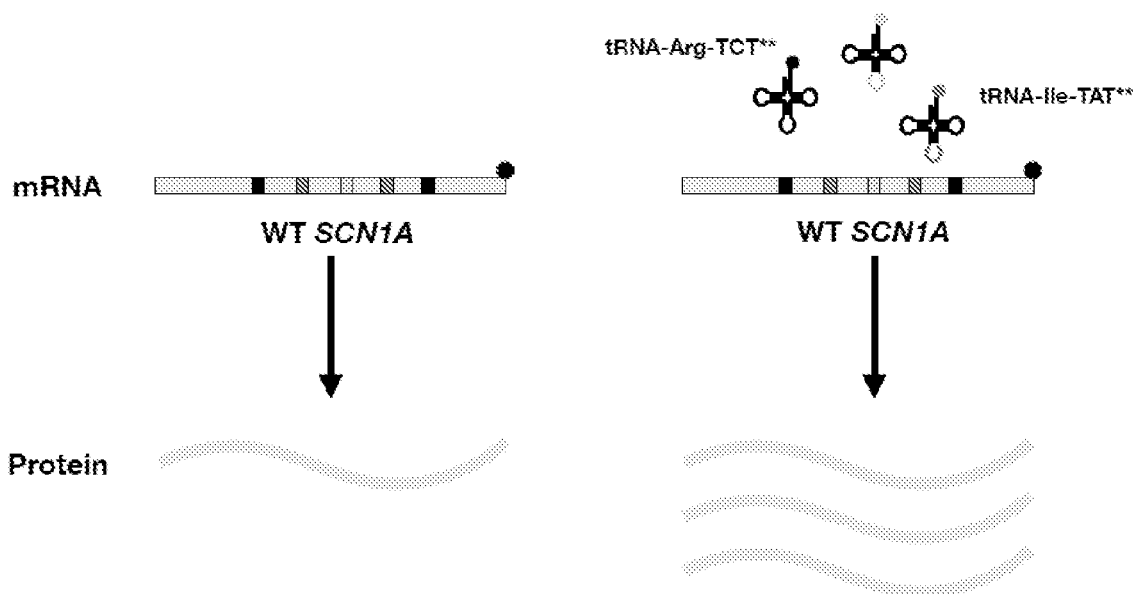
FIG. 1 is a schematic representation of SCN1A mRNA transcripts containing non-optimal codons that destabilize the mRNA transcript. Non-optimal codons are indicated as darker regions in the otherwise grey transcript. Expression of the indicated tRNAs stabilizes the mRNA transcript and facilitates increased expression of the protein.

This disclosure relates generally to methods and compositions for increasing expression of a gene product encoded by a gene containing a non-optimal codon and/or treating a haploinsufficiency disorder in a subject. The presence of the non-optimal codon in the gene of interest results in a destabilization of mRNA transcribed from the gene, which can impact the production of functional protein encoded by the gene. Under such situations, destabilization of the mRNA transcript can occur when, for example, the abundance of a specific aminoacylated tRNA molecule that hybridizes to the non-optimal codon is lower than other, different tRNAs available in a cell that are aminoacylated with the same amino acid. Without wishing to be bound by theory, it is believed that, given the lower abundance of the specific tRNAs, it can take longer for those available tRNAs to reach and be taken up by the ribosome during protein synthesis than other more abundant tRNAs, which in turn can create a lag in the synthesis of the protein during the incorporation of the requisite amino acid at that position. The lag in the rate of protein synthesis is believed to induce a corresponding destabilization of the mRNA transcript, which can result in reduced production of the protein encoded by the mRNA transcript. It has been discovered that increasing the abundance of such tRNAs in the cell of interest relative to the other, naturally more abundant tRNAs can promote the expression and/or amount of functional protein produced by the cell.

Expression of a gene product, namely, a product that results of the expression of a gene, e.g., an mRNA transcript encoded by the gene, a protein encoded by the gene, etc., can be increased and/or selectively increased (e.g., the expression of the gene product can be increased more than another gene product or more than any other gene product) by the introduction into the cell of a minimal number (e.g., 1, 2, or 3) of tRNAs that decode non-optimal codons in the gene.

Similarly, for a subject having a gene containing a non-optimal codon, administration to the subject of an effective amount of a tRNA that decodes the non-optimal codon can increase expression of a gene product from the gene in the subject. Accordingly, administration of the tRNA to the subject can treat a disease in the subject that is mediated by insufficient expression of the gene product, for example, a haploinsufficiency disorder. In addition, features of the methods and compositions described herein can make them desirable for use in treatment of disorders, e.g., haploinsufficiency disorders, in human subjects. For example, tRNAs are relatively small in size and can be produced recombinantly, and the methods and compositions described herein can treat a haploinsufficiency disorder regardless of the mutation or mechanism by which an allele was inactivated.

Accordingly, in one aspect, this disclosure provides a method of increasing expression in a mammalian cell of a gene product encoded by a gene containing a first non-optimal codon. The method includes introducing into the cell an effective amount of a first exogenous tRNA that (i) comprises an anticodon that hybridizes to the first non-optimal codon, and (ii) is capable of being aminoacylated with an amino acid, wherein introduction of the first exogenous tRNA into the cell increases the expression of the gene product relative to a similar cell lacking the first exogenous tRNA.

In another aspect, this disclosure provides a method of increasing expression in a mammalian cell of a gene product encoded by a gene containing a first non-optimal codon. The method includes introducing into the cell an effective amount of a first expression vector capable of expressing a first exogenous tRNA that (i) comprises an anticodon that hybridizes to the first non-optimal codon, and (ii) is capable of being aminoacylated with an amino acid, wherein expression of the first exogenous tRNA in the cell increases the expression of the gene product relative to a similar cell lacking the first exogenous tRNA.

It is further contemplated that, in any of the foregoing methods, the gene may contain an additional non-optimal codon (e.g., a second, third, fourth, fifth, sixth, seventh, eighth, ninth, or tenth non-optimal codon) and the method further may comprise introducing to cell an effective amount of an additional exogenous tRNA or expression vector (e.g., a second, third, fourth, fifth, sixth, seventh, eighth, ninth, or tenth exogenous tRNA or expression vector) to increase expression of the gene product.

For example, in certain embodiments, if the gene contains a second and/or third non-optimal codon, the method further comprises introducing into the cell an effective amount of a second and/or third exogenous tRNA that (i) comprises an anticodon that hybridizes to the second and/or third non-optimal codon, and (ii) is capable of being aminoacylated with an amino acid, wherein introduction of the second and/or third exogenous tRNA into the cell increases the expression of the gene product relative to a similar cell lacking the second and/or third exogenous tRNA. In certain embodiments, if gene contains a second and/or third non-optimal codon, the method further comprises introducing into the cell an effective amount of a second and/or third expression vector capable of expressing a second and/or third exogenous tRNA that (i) comprises an anticodon that hybridizes to the second and/or third non-optimal codon, and (ii) is capable of being aminoacylated with an amino acid, wherein expression of the second and/or third exogenous tRNA in the cell increases the expression of the gene product relative to a similar cell lacking the second and/or third exogenous tRNA.

In certain embodiments, the method increases the expression of the gene product in a cell, tissue, or subject by at least about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, about 500%, about 600%, about 700%, about 800%, about 900%, about 1000%, or more relative to a cell, tissue, or subject lacking the exogenous tRNA. In certain embodiments, the method increases the expression of the gene product in a cell, tissue, or subject by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 200%, about 160% to about 180%, or about 180% to about 200% relative to a cell, tissue, or subject lacking the exogenous tRNA. In certain embodiments, the method increases the expression of the gene product in a cell, tissue, or subject by from about 100% to about 1000%, about 100% to about 900%, about 100% to about 800%, about 100% to about 700%, about 100% to about 600%, about 100% to about 500%, about 100% to about 400%, about 100% to about 300%, about 100% to about 200%, about 200% to about 1000%, about 200% to about 900%, about 200% to about 800%, about 200% to about 700%, about 200% to about 600%, about 200% to about 500%, about 200% to about 400%, about 200% to about 300%, about 300% to about 1000%, about 300% to about 900%, about 300% to about 800%, about 300% to about 700%, about 300% to about 600%, about 300% to about 500%, about 300% to about 400%, about 400% to about 1000%, about 400% to about 900%, about 400% to about 800%, about 400% to about 700%, about 400% to about 600%, about 400% to about 500%, about 500% to about 1000%, about 500% to about 900%, about 500% to about 800%, about 500% to about 700%, about 500% to about 600%, about 600% to about 1000%, about 600% to about 900%, about 600% to about 800%, about 600% to about 700%, about 700% to about 1000%, about 700% to about 900%, about 700% to about 800%, about 800% to about 1000%, about 800% to about 900%, or about 900% to about 1000% relative to a cell, tissue, or subject lacking the exogenous tRNA. Gene product or protein expression may be measured by any method known in the art, for example, Western blot or ELISA.

In certain embodiments, the method increases the stability of a gene transcript (mRNA) encoded by the gene in a cell, tissue, or subject relative to a similar cell, tissue, or subject lacking the exogenous tRNA. For example, in certain embodiments, the method increases the mRNA stability in the cell, tissue, or subject by at least about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, about 500%, about 600%, about 700%, about 800%, about 900%, about 1000%, or more relative to a cell, tissue, or subject lacking the exogenous tRNA. In certain embodiments, the method increases the mRNA stability in the cell, tissue, or subject by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 200%, about 160% to about 180%, or about 180% to about 200% relative to a cell, tissue, or subject lacking the exogenous tRNA. In certain embodiments, the method increases the mRNA stability in the cell, tissue, or subject by from about 100% to about 1000%, about 100% to about 900%, about 100% to about 800%, about 100% to about 700%, about 100% to about 600%, about 100% to about 500%, about 100% to about 400%, about 100% to about 300%, about 100% to about 200%, about 200% to about 1000%, about 200% to about 900%, about 200% to about 800%, about 200% to about 700%, about 200% to about 600%, about 200% to about 500%, about 200% to about 400%, about 200% to about 300%, about 300% to about 1000%, about 300% to about 900%, about 300% to about 800%, about 300% to about 700%, about 300% to about 600%, about 300% to about 500%, about 300% to about 400%, about 400% to about 1000%, about 400% to about 900%, about 400% to about 800%, about 400% to about 700%, about 400% to about 600%, about 400% to about 500%, about 500% to about 1000%, about 500% to about 900%, about 500% to about 800%, about 500% to about 700%, about 500% to about 600%, about 600% to about 1000%, about 600% to about 900%, about 600% to about 800%, about 600% to about 700%, about 700% to about 1000%, about 700% to about 900%, about 700% to about 800%, about 800% to about 1000%, about 800% to about 900%, or about 900% to about 1000% relative to a cell, tissue, or subject lacking the exogenous tRNA. Gene transcript or mRNA stability may be measured by any method known in the art, for example, Northern blot.

In certain embodiments, the cell is a human cell. In certain embodiments, the cell is a central nervous system cell, e.g., a neuron.

In certain embodiments, the gene is selected from AGGF1, ARHGAP31, BMPR2, CHD7, COL2A1, COL3A1, CTLA4, CTNNB1, DLL4, EHMT1, ELN, ENG, FAS, FBN1, FOXG1, GATA3, GLI3, GRN, IRF6, JAG1, KCNQ4, LMX1B, MBD5, MED13L, MITF, MNX1, MYCN, NFIA, NFIX, NOTCH1, NSD1, PAX3, PHIP, PRKAR1A, RAI1, RBPJ, RPS14, RUNX2, SALL4, SCN1A, SETBP1, SHANK3, SHH, SHOX, SLC2A1/GLUT1, SOX10, SYNGAP1, TBX1, TBX3, TBX5, TCF4, TCOF1, TGIF1, TNXB, TRPS1, WT1, and ZIC2. In certain embodiments, the gene is SCN1A.

In certain embodiments, the method does not substantially increase the expression of a gene product from a reference gene. For example, in certain embodiments, the method increases the expression of the gene product from the reference gene by less than about 5%, about 10%, about 20%, about 30%, about 40%, or about 50%. In certain embodiments, there is no detectable increase in the expression of the reference gene. In certain embodiments, the reference gene is selected from GAPDH, BAD and TRAPPC6A. In certain embodiments, the reference gene is GAPDH.

In certain embodiments, wherein the gene is a SCN1A gene, the method increases voltage-gated sodium channel activity in a cell, tissue, or subject by at least about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 250%, about 300%, about 350%, about 400%, about 450%, about 500%, about 600%, about 700%, about 800%, about 900%, about 1000%, or more relative to a cell, tissue, or subject lacking the exogenous tRNA. In certain embodiments, the method increases voltage-gated sodium channel activity in a cell, tissue, or subject by from about 20% to about 200%, about 20% to about 180%, about 20% to about 160%, about 20% to about 140%, about 20% to about 120%, about 20% to about 100%, about 20% to about 80%, about 20% to about 60%, about 20% to about 40%, about 40% to about 200%, about 40% to about 180%, about 40% to about 160%, about 40% to about 140%, about 40% to about 120%, about 40% to about 100%, about 40% to about 80%, about 40% to about 60%, about 60% to about 200%, about 60% to about 180%, about 60% to about 160%, about 60% to about 140%, about 60% to about 120%, about 60% to about 100%, about 60% to about 80%, about 80% to about 200%, about 80% to about 180%, about 80% to about 160%, about 80% to about 140%, about 80% to about 120%, about 80% to about 100%, about 100% to about 200%, about 100% to about 180%, about 100% to about 160%, about 100% to about 140%, about 100% to about 120%, about 120% to about 200%, about 120% to about 180%, about 120% to about 160%, about 120% to about 140%, about 140% to about 200%, about 140% to about 180%, about 140% to about 160%, about 160% to about 200%, about 160% to about 180%, or about 180% to about 200% relative to a cell, tissue, or subject lacking the exogenous tRNA. Voltage-gated sodium channel activity may be measured by any method known in the art, for example, as described in Kalume et al. (2007) J. NEUROSCI. 27 (41): 11065-74, Yu et al. (2007) NAT. NEUROSCI. 9 (9): 1142-9, and Han et al. (2012) NATURE 489 (7416): 385-390.

In certain embodiments, the haploinsufficiency disorder is a disorder listed in TABLE 1 or TABLE 2, and the haploinsufficient gene is a gene listed in the corresponding row of TABLE 1 or TABLE 2. In certain embodiments, the gene is a gene listed in TABLE 1 or TABLE 2, and the first, second, and/or third non-optimal codon is a codon listed in the corresponding row of TABLE 1 or TABLE 2. In certain embodiments, the haploinsufficiency disorder is a disorder listed in TABLE 1 or TABLE 2, and the first, second, and/or third non-optimal codon is a codon listed in the corresponding row of TABLE 1 or TABLE 2.

TABLE 1

| Disorder | Gene | Codons |
|---|---|---|
| 5q-syndrome | RPS14 | GGT (Gly), CGC (Arg), ACC (Thr), CTC (Leu), CCT (Pro) |
| Adams-Oliver syndrome 1 | ARHGAP31 | TCA (Ser), GAG (Glu), AGC (Ser), CCC (Pro), CCT (Pro), CTC (Leu) |
| Adams-Oliver syndrome 3 | RBPJ | ACA (Thr), TCA (Ser), TTT (Phe), CTT (Leu), CCT (Pro), TAT (Tyr) |
| Adams-Oliver syndrome 5 | NOTCH1 | CCC (Pro), CTG (Leu), GGC (Gly), TGC (Cys), CTC (Leu) |
| Adams-Oliver syndrome 6 | DLL4 | CGC (Arg), CTG (Leu), ACC (Thr), CCC (Pro), TGT (Cys), TGC (Cys) |
| Alagille syndrome 1 | JAG1 | TGT (Cys), GAT (Asp), CCC (Pro), TGC (Cys) |
| Autoimmune lymphoproliferative syndrome type IA | FAS | CAT (His), AGA (Arg), GAA (Glu), CTT (Leu) |
| Autoimmune lymphoproliferative syndrome type V | CTLA4 | TTT (Phe), CTC (Leu), CCA (Pro), CTT (Leu), TAT (Tyr) |
| Autosomal dominant deafness-2A | KCNQ4 | CGC (Arg), CTG (Leu), TCC (Ser), CTC (Leu), CCC (Pro) |
| Brain malformations with or without urinary tract defects (BRMUTD) | NFIA | AGT (Ser), CCA (Pro), ACA (Thr), CCC (Pro), CTC (Leu), CCA (Pro) |
| Carney complex type 1 | PRKAR1A | GAT (Asp), TTT (Phe), GAG (Glu), AGA (Arg), CTC (Leu), CTT (Leu) |
| CHARGE syndrome | CHD7 | GAT (Asp), TCA (Ser), GAA (Glu), CCT (Pro), AGA (Arg), CTC (Leu) |
| Cleidocranial dysplasia | RUNX2 | CCC (Pro), CCG (Pro), TCC (Ser), CTC (Leu), CCT (Pro) |
| Currarino syndrome | MNX1 | GCG (Ala), GGC (Gly), CCG (Pro), CCC (Pro), CTC (Leu) |
| Denys-Drash syndrome / Frasier syndrome | WT1 | CCC (Pro), CCG (Pro), AGC (Ser), AGA (Arg) |
| Developmental delay, intellectual disability, obesity, and dysmorphic features (DIDOD) | PHIP | GAT (Asp), TCA (Ser), AGT (Ser), AGA (Arg), ATA (Ile), CTT (Leu) |
| DiGeorge syndrome (TBX1-associated) | TBX1 | CCG (Pro), CCC (Pro), GCG (Ala), GCC (Ala) |
| Dravet syndrome | SCN1A | TTT (Phe), CTA (Leu), GAT (Asp), ATA (Ile), AGA (Arg), CTT (Leu) |
| Duane-radial ray syndrome | SALL4 | ACC (Thr), AGC (Ser), TCC (Ser), CCC (Pro), CTC (Leu), CCT (Pro) |
| Ehlers-Danlos syndrome (classic-like) | TNXB | CCC (Pro), CGC (Arg), GAG (Glu), CTC (Leu), CCT (Pro) |
| Ehlers-Danlos syndrome (vascular type) | COL3A1 | GGT (Gly), GGA (Gly), CCT (Pro), CCC (Pro) |
| Feingold syndrome 1 | MYCN | CCC (Pro), CCG (Pro), GAG (Glu), CTC (Leu) |
| Frontotemporal lobar degeneration with TDP43 inclusions (FTLD-TDP), GRN-related | GRN | CCC (Pro), ACC (Thr), CAC (His), TGC (Cys), TGT (Cys) |
| GLUT1 deficiency syndrome | SLC2A1 | CTG (Leu), TTC (Phe), CCC (Pro), CTC (Leu), ATC (Ile) |

TABLE 1-continued

| Disorder | Gene | Codons |
|---|---|---|
| Greig cephalopolysyndactyly syndrome | GLI3 | AGC (Ser), TCC (Ser), CAT (His), CCC (Pro), CTC (Leu) |
| Hereditary hemorrhagic telangiectasia type 1 | ENG | AGC (Ser), CTG (Leu), CTC (Leu), CCC (Pro), TCC (Ser) |
| Holoprosencephaly 3 | SHH | CTG (Leu), CGC (Arg), GCG (Ala), CTC (Leu), CCC (Pro) |
| Holoprosencephaly 4 | TGIF1 | TCC (Ser), CCA (Pro), CTA (Leu), CTC (Leu), CCC (Pro) |
| Holoprosencephaly 5 | ZIC2 | GCG (Ala), CAC (His), GGC (Gly), CCC (Pro), CTC (Leu) |
| Holt-Oram syndrome | TBX5 | TCC (Ser), CCC (Pro), CAT (His), CCT (Pro), CTC (Leu) |
| Hypoparathyroidism, sensorineural deafness, and renal disease (HDR) | GATA3 | TCC (Ser), CCC (Pro), CAC (His), CTC (Leu) |
| Kleefstra syndrome 1 | EHMT1 | GAG (Glu), CTG (Leu), AGC (Ser), CCC (Pro), CTC (Leu) |
| Klippel-Trenaunay syndrome (AAGF-related) | AGGF1 | GAT (Asp), AGT (Ser), GAA (Glu), AGA (Arg), TAT (Tyr) |
| Leri-Weill dyschondrosteosis | SHOX | CTG (Leu), CGC (Arg), GAG (Glu), CTC (Leu), CCC (Pro) |
| Marfan syndrome | FBN1 | GAT (Asp), TGT (Cys), GGA (Gly), TGC (Cys), CCC (Pro) |
| Mental retardation and distinctive facial features with or without cardiac defects (MRFACD) | MED13L | GAT (Asp), AGT (Ser), TCA (Ser), CTC (Leu), CCC (Pro), CCT (Pro) |
| Mental retardation, autosomal dominant 1 | MBD5 | AGT (Ser), TCA (Ser), CCA (Pro), CCT (Pro), AGA (Arg), CCC (Pro) |
| Mental retardation, autosomal dominant 19 | CTNNB1 | GAT (Asp), GGT (Gly), CAT (His), CTT (Leu), CTC (Leu), TAT (Tyr) |
| Mental retardation, autosomal dominant 29 | SETBP1 | AGT (Ser), CCA (Pro), CCC (Pro), CTC (Leu), CCT (Pro) |
| Nail-patella syndrome (NPS) | LMX1B | TCC (Ser), CTG (Leu), GAG (Glu), CCC (Pro), CTC (Leu) |
| Phelan-McDermid syndrome | SHANK3 | CGC (Arg), CCC (Pro), CTG (Leu), CTC (Leu) |
| Pitt-Hopkins syndrome | TCF4 | TCA (Ser), CAT (His), AGT (Ser), CCT (Pro), CTC (Leu), AGA (Arg) |
| Primary pulmonary hypertension 1 | BMPR2 | ACA (Thr), TCA (Ser), GAT (Asp), AGA (Arg), CTT (Leu), ATA (Ile) |
| Rett syndrome (congenital variant) | FOXG1 | CCG (Pro), CCC (Pro), CAC (His), CTC (Leu) |
| Smith-Magenis syndrome (RAI1-associated) | RAI1 | CCC (Pro), TCC (Ser), AGC (Ser), CTC (Leu) |
| Sotos syndrome 1 | NSD1 | TCA (Ser), GAT (Asp), AGT (Ser), CCT (Pro), AGA (Arg), CCC (Pro) |
| Sotos syndrome 2 | NFIX | TCC (Ser), CTG (Leu), TCA (Ser), CCC (Pro), CCT (Pro) |
| Stickler syndrome type I | COL2A1 | GGT (Gly), CCT (Pro), GGA (Gly), CCC (Pro) |
| Supravalvular aortic stenosis | ELN | GGA (Gly), GGT (Gly), GCA (Ala), CCT (Pro), CCC (Pro) |
| SYNGAP1-related intellectual disability | SYNGAP1 | CTG (Leu), GAG (Glu), CGG (Arg), CCC (Pro), CTC (Leu) |

TABLE 1-continued

| Disorder | Gene | Codons |
|---|---|---|
| Treacher Collins syndrome | TCOF1 | TCA (Ser), GAG (Glu), AGT (Ser), CCC (Pro), CCT (Pro) |
| Trichorhinophalangeal syndrome type I | TRPS1 | AGT (Ser), TCA (Ser), CAT (His), AGA (Arg), CCT (Pro), CCC (Pro) |
| Ulnar-mammary syndrome | TBX3 | TCC (Ser), GCG (Ala), CCG (Pro), CCC (Pro), CTC (Leu), TCC (Ser) |
| van der Woude syndrome 1 | IRF6 | CCC (Pro), CTG (Leu), GAT (Asp), CTC (Leu), CCT (Pro) |
| Waardenburg syndrome type 1 | PAX3 | AGC (Ser), ACC (Thr), CCC (Pro), CTC (Leu), CCT (Pro) |
| Waardenburg syndrome type 2A | MITF | TCC (Ser), CAT (His), CAA (Gln), CCC (Pro), CTC (Leu), CTT (Leu) |
| Waardenburg syndrome type 4C | SOX10 | CCC (Pro), GAG (Glu), TCA (Ser), CTC (Leu) |

TABLE 2

| Disorder | Gene | Codons |
|---|---|---|
| 5q-syndrome | RPS14 | GGT (Gly), CGC (Arg), ACC (Thr), GTC (Val), GAT (Asp), GGA (Gly), TTT (Phe), GAA (Glu), CAT (His), AGG (Arg), CTC (Leu), CCT (Pro), CCC (Pro), ATC (Ile), CTT (Leu), AAG (Lys), GCC (Ala) |
| Adams-Oliver syndrome 1 | ARHGAP31 | TCA (Ser), GAG (Glu), AGC (Ser), CCA (Pro), CTG (Leu), CCC (Pro), CCT (Pro), ACC (Thr), TCC (Ser), AGG (Arg), CTC (Leu), AGA (Arg), CTT (Leu), GAA (Glu), GCA (Ala) |
| Adams-Oliver syndrome 3 | RBPJ | ACA (Thr), TCA (Ser), TTT (Phe), GAT (Asp), AGT (Ser), CCA (Pro), CGA (Arg), CAT (His), GTA (Val), GGA (Gly), CTT (Leu), CCT (Pro), TAT (Tyr), ATA (Ile), AGA (Arg), GCA (Ala), CTC (Leu), GAA (Glu) |
| Adams-Oliver syndrome 5 | NOTCH1 | CCC (Pro), CTG (Leu), GGC (Gly), ACC (Thr), CGC (Arg), GAG (Glu), AGC (Ser), GAC (Asp), TCC (Ser), CCG (Pro), TGC (Cys), CTC (Leu), TGT (Cys), TAC (Tyr), AAC (Asn), GCC (Ala) |
| Adams-Oliver syndrome 6 | DLL4 | CGC (Arg), CTG (Leu), ACC (Thr), GGC (Gly), CCC (Pro), TCC (Ser), AGC (Ser), CGG (Arg), TGT (Cys), CCA (Pro), TGC (Cys), CTC (Leu), CCT (Pro), TAC (Tyr), TAT (Tyr), GAG (Glu) |
| Alagille syndrome 1 | JAG1 | TGT (Cys), GAT (Asp), CCC (Pro), AGT (Ser), ACC (Thr), TCC (Ser), GGC (Gly), GAC (Asp), GAG (Glu), TCA (Ser), TGC (Cys), CTC (Leu), CCT (Pro), AGA (Arg), TAT (Tyr), AAC (Asn), AAT (Asn) |
| Autoimmune lymphoproliferative syndrome type IA | FAS | CAT (His), AGA (Arg), GAA (Glu), ACA (Thr), CAA (Gln), ACC (Thr), TTG (Leu), ACT (Thr), CTA (Leu), GTT (Val), CTT (Leu), TGT (Cys), CTC (Leu), AAT (Asn), TGC (Cys), ATA (Ile), CCT (Pro) |
| Autoimmune lymphoproliferative syndrome type V | CTLA4 | TTT (Phe), CTC (Leu), CCA (Pro), ACC (Thr), ACA (Thr), AGC (Ser), TAT (Tyr), CTA (Leu), CTG (Leu), GAT (Asp), CTT (Leu), CCC (Pro), CCT (Pro), GCA (Ala), TAC (Tyr), TGC (Cys) |
| Autosomal dominant deafness-2A | KCNQ4 | CGC (Arg), CTG (Leu), TCC (Ser), CGG (Arg), AGC (Ser), CCC (Pro), GGC (Gly), ACC (Thr), GTC (Val), GAG (Glu), CTC (Leu), TAC (Tyr), ATC (Ile), GCC (Ala), CCT (Pro) |

TABLE 2-continued

| Disorder | Gene | Codons |
|---|---|---|
| Brain malformations with or without urinary tract defects (BRMUTD) | NFIA | AGT (Ser), CCA (Pro), ACA (Thr), TCA (Ser), CAT (His), CCC (Pro), TTT (Phe), TCC (Ser), CGC (Arg), GAT (Asp), CTC (Leu), CCT (Pro), CTT (Leu), GCA (Ala), AGA (Arg) |
| Carney complex type 1 | PRKAR1A | GAT (Asp), TTT (Phe), GAG (Glu), AGA (Arg), TCA (Ser), GAA (Glu), AGT (Ser), CGA (Arg), GCA (Ala), CGT (Arg), CTC (Leu), CTT (Leu), TAT (Tyr), CCT (Pro), CCC (Pro) |
| CHARGE syndrome | CHD7 | GAT (Asp), TCA (Ser), GAA (Glu), TTT (Phe), CCA (Pro), AGT (Ser), GAG (Glu), CTA (Leu), CAT (His), CAA (Gln), CCT (Pro), AGA (Arg), CTC (Leu), CCC (Pro), CTT (Leu), ATA (Ile), GCA (Ala) |
| Cleidocranial dysplasia | RUNX2 | CCC (Pro), CCG (Pro), TCC (Ser), ACC (Thr), GCG (Ala), CGC (Arg), CTG (Leu), CGG (Arg), AGC (Ser), AGT (Ser), CTC (Leu), CCT (Pro), AGA (Arg), GCA (Ala) |
| Currarino syndrome | MNX1 | GCG (Ala), GGC (Gly), CCG (Pro), CTG (Leu), CGC (Arg), CCC (Pro), TCG (Ser), GCC (Ala), AGC (Ser), GAG (Glu), CTC (Leu), TCC (Ser) |
| Denys-Drash syndrome/ Frasier syndrome | WT1 | CCC (Pro), CCG (Pro), AGC (Ser), CAC (His), GCG (Ala), CTG (Leu), ACC (Thr), TCC (Ser), CAT (His), GGT (Gly), AGA (Arg), TAC (Tyr), TGT (Cys), CTC (Leu), CCT (Pro) |
| Developmental delay, intellectual disability, obesity, and dysmorphic features (DIDOD) | PHIP | GAT (Asp), TCA (Ser), AGT (Ser), AGA (Arg), CAT (His), ATA (Ile), TTT (Phe), CTA (Leu), GAA (Glu), CAA (Gln), CTT (Leu), CCT (Pro), TAT (Tyr), GCA (Ala), CCC (Pro) |
| DiGeorge syndrome (TBX1-associated) | TBX1 | CCG (Pro), CCC (Pro), GCG (Ala), GCC (Ala), CAC (His), CTG (Leu), GGC (Gly), CGC (Arg), AGC (Ser), CGG (Arg), CTC (Leu), TAC (Tyr), TAT (Tyr), GAG (Glu), TTC (Phe) |
| Dravet syndrome | SCN1A | TTT (Phe), CTA (Leu), GAT (Asp), AGT (Ser), GAA (Glu), ATA (Ile), TCA (Ser), ACA (Thr), TTC (Phe), TAT (Tyr), AGA (Arg), CTT (Leu), CTC (Leu), AAT (Asn), CCT (Pro) |
| Duane-radial ray syndrome | SALL4 | ACC (Thr), AGC (Ser), TCC (Ser), CCC (Pro), GAG (Glu), GGT (Gly), GAT (Asp), CTC (Leu), CAC (His), CAG (Gln), CCT (Pro), TGT (Cys), ATC (Ile), CTT (Leu) |
| Ehlers-Danlos syndrome (classic-like) | TNXB | CCC (Pro), CGC (Arg), GAG (Glu), ACC (Thr), CTG (Leu), ACA (Thr), GGG (Gly), TCC (Ser), GGC (Gly), GTG (Val), CTC (Leu), CCT (Pro), TAC (Tyr) |
| Ehlers-Danlos syndrome (vascular type) | COL3A1 | GGT (Gly), GGA (Gly), CCT (Pro), CCA (Pro), GAT (Asp), AGT (Ser), GAA (Glu), CCC (Pro), GGC (Gly), AGA (Arg), CTT (Leu), CTC (Leu), GCA (Ala) |
| Feingold syndrome 1 | MYCN | CCC (Pro), CCG (Pro), GAG (Glu), CGC (Arg), TCC (Ser), AGC (Ser), GCC (Ala), ACC (Thr), CTG (Leu), GAT (Asp), CTC (Leu), GCG (Ala), CTT (Leu), AAG (Lys) |
| Frontotemporal lobar degeneration with TDP43 inclusions (FTLD-TDP), GRN-related | GRN | CCC (Pro), ACC (Thr), CAC (His), TCC (Ser), GAT (Asp), TGC (Cys), CTG (Leu), TGT (Cys), AGC (Ser), CGC (Arg), CCT (Pro), CTC (Leu), AGA (Arg), GCC (Ala) |
| GLUT1 deficiency syndrome | SLC2A1 | CTG (Leu), TTC (Phe), CCC (Pro), TCC (Ser), GGC (Gly), CGC (Arg), ACC (Thr), ATC (Ile), CTC (Leu), GTG (Val), GAG (Glu), TAT (Tyr), GCC (Ala) |

TABLE 2-continued

| Disorder | Gene | Codons |
|---|---|---|
| Greig cephalopolysyndactyly syndrome | GLI3 | AGC (Ser), TCC (Ser), CAT (His), CCC (Pro), TCA (Ser), CCG (Pro), ACC (Thr), CCA (Pro), CTC (Leu), CTG (Leu), CCT (Pro), AGA (Arg), CTT (Leu), GAG (Glu) |
| Hereditary hemorrhagic telangiectasia type 1 | ENG | AGC (Ser), CTG (Leu), CTC (Leu), ACC (Thr), CCC (Pro), TCC (Ser), GTC (Val), GAG (Glu), TCA (Ser), GGC (Gly), CTT (Leu), ATC (Ile), GCC (Ala) |
| Holoprosencephaly 3 | SHH | CTG (Leu), CGC (Arg), GCG (Ala), TCG (Ser), ACC (Thr), GGC (Gly), GAG (Glu), CTC (Leu), GAC (Asp), CAC (His), CCC (Pro), TAC (Tyr), GCC (Ala), AGA (Arg) |
| Holoprosencephaly 4 | TGIF1 | TCC (Ser), CCA (Pro), CTA (Leu), CCG (Pro), TCA (Ser), CGC (Arg), CCC (Pro), ACA (Thr), TCT (Ser), CTC (Leu), CTT (Leu), CCT (Pro), AGA (Arg) |
| Holoprosencephaly 5 | ZIC2 | GCG (Ala), CAC (His), GGC (Gly), TCC (Ser), CCG (Pro), CCC (Pro), AGC (Ser), CGC (Arg), TCG (Ser), TTC (Phe), CTC (Leu), GAG (Glu) |
| Holt-Oram syndrome | TBX5 | TCC (Ser), CCC (Pro), CAT (His), ACC (Thr), AGC (Ser), CAC (His), CTA (Leu), TTT (Phe), CCT (Pro), GAG (Glu), CTC (Leu), TAC (Tyr), AGA (Arg), CCA (Pro) |
| Hypoparathyroidism, sensorineural deafness, and renal disease (HDR) | GATA3 | TCC (Ser), CCC (Pro), CAC (His), CCG (Pro), ACC (Thr), TCG (Ser), AGC (Ser), CTG (Leu), CTC (Leu), AGG (Arg), TAC (Tyr), AGA (Arg) |
| Kleefstra syndrome 1 | EHMT1 | GAG (Glu), CTG (Leu), AGC (Ser), CCC (Pro), GAC (Asp), CTC (Leu), ACC (Thr), TCC (Ser), AGG (Arg), TCA (Ser), GCA (Ala), TGC (Cys), GCC (Ala), AGA (Arg), CTT (Leu), CCT (Pro) |
| Klippel-Trenaunay syndrome (AAGF-related) | AGGF1 | GAT (Asp), AGT (Ser), GAA (Glu), TCA (Ser), CAT (His), ACA (Thr), TAT (Tyr), CAA (Gln), TTT (Phe), ACT (Thr), AGA (Arg), CCT (Pro), CTT (Leu), CTC (Leu), AAT (Asn), GAG (Glu), GCA (Ala) |
| Leri-Weill dyschondrosteosis | SHOX | CTG (Leu), CGC (Arg), GAG (Glu), GCG (Ala), CTC (Leu), CAC (His), TCC (Ser), AGC (Ser), CGG (Arg), GCC (Ala), CCC (Pro), AGA (Arg), CCG (Pro) |
| Marfan syndrome | FBN1 | GAT (Asp), TGT (Cys), GGA (Gly), GAA (Glu), AGT (Ser), ACA (Thr), ACC (Thr), TTT (Phe), CCA (Pro), AAT (Asn), TGC (Cys), CCC (Pro), CCT (Pro), AGA (Arg), CTC (Leu), TAT (Tyr) |
| Mental retardation and distinctive facial features with or without cardiac defects (MRFACD) | MED13L | GAT (Asp), AGT (Ser), TCA (Ser), CCA (Pro), TTT (Phe), ACA (Thr), CCC (Pro), CAT (His), CCT (Pro), CTA (Leu), CTC (Leu), CTT (Leu), AGA (Arg), ATA (Ile), GCA (Ala), TAT (Tyr), TCC (Ser) |
| Mental retardation, autosomal dominant 1 | MBD5 | AGT (Ser), TCA (Ser), CCA (Pro), CTA (Leu), CAT (His), ACA (Thr), CCT (Pro), TTA (Leu), GGA (Gly), CAA (Gln), AGA (Arg), CCC (Pro), CTC (Leu), CTT (Leu), ATA (Ile), AAT (Asn), GCA (Ala) |
| Mental retardation, autosomal dominant 19 | CTNNB1 | GAT (Asp), GGT (Gly), CAT (His), ACA (Thr), CTT (Leu), CAA (Gln), CTG (Leu), CTA (Leu), GAA (Glu), TCT (Ser), CTC (Leu), TAT (Tyr), CCT (Pro), AGA (Arg), GCA (Ala), ATA (Ile), GGA (Gly) |
| Mental retardation, autosomal dominant 29 | SETBP1 | AGT (Ser), CCA (Pro), CCC (Pro), TCC (Ser), AGC (Ser), TCA (Ser), ACC (Thr), GAG (Glu), CTG (Leu), AGG (Arg), CTC (Leu), CCT (Pro), AGA (Arg), CTT (Leu), GCA (Ala), AAG (Lys) |

TABLE 2-continued

| Disorder | Gene | Codons |
|---|---|---|
| Nail-patella syndrome (NPS) | LMX1B | TCC (Ser), CTG (Leu), GAG (Glu), CCC (Pro), AGC (Ser), CGG (Arg), CAG (Gln), CGC (Arg), CTC (Leu), GAC (Asp), TGC (Cys), TAC (Tyr), AAG (Lys), AGA (Arg), CCG (Pro) |
| Phelan-McDermid syndrome | SHANK3 | CGC (Arg), CCC (Pro), CTG (Leu), CCG (Pro), GAG (Glu), AGC (Ser), TCC (Ser), CGG (Arg), CTC (Leu), GGC (Gly), CCT (Pro), GCC (Ala), GCG (Ala) |
| Pitt-Hopkins syndrome | TCF4 | TCA (Ser), CAT (His), AGT (Ser), TCC (Ser), CCA (Pro), AGC (Ser), TCT (Ser), GGA (Gly), GAT (Asp), CCT (Pro), CTC (Leu), AGA (Arg), CCC (Pro), TAT (Tyr), CTT (Leu) |
| Primary pulmonary hypertension 1 | BMPR2 | ACA (Thr), TCA (Ser), GAT (Asp), CAT (His), AGT (Ser), GAA (Glu), CCA (Pro), CTA (Leu), ATA (Ile), ACT (Thr), AGA (Arg), CTT (Leu), CCC (Pro), CCT (Pro), TAT (Tyr), CTC (Leu), GCA (Ala), AAT (Asn) |
| Rett syndrome (congenital variant) | FOXG1 | CCG (Pro), CCC (Pro), CAC (His), TCC (Ser), CTG (Leu), TCG (Ser), GGC (Gly), CGC (Arg), AGC (Ser), ACC (Thr), CTC (Leu), TAC (Tyr), GCC (Ala), GAG (Glu), GCG (Ala), |
| Smith-Magenis syndrome (RAI1-associated) | RAI1 | CCC (Pro), TCC (Ser), AGC (Ser), CTG (Leu), ACC (Thr), GAG (Glu), CTC (Leu), CCG (Pro), CGG (Arg), CCA (Pro), CCT (Pro), GCC (Ala), AAG (Lys) |
| Sotos syndrome 1 | NSD1 | TCA (Ser), GAT (Asp), AGT (Ser), CCA (Pro), TTT (Phe), CTA (Leu), GAA (Glu), TCT (Ser), CAT (His), GAG (Glu), CCT (Pro), AGA (Arg), CCC (Pro), CTT (Leu), CTC (Leu), TGT (Cys), ATA (Ile) |
| Sotos syndrome 2 | NFIX | TCC (Ser), CTG (Leu), TCA (Ser), CCC (Pro), CGG (Arg), CCG (Pro), ACC (Thr), CGC (Arg), GAT (Asp), TTT (Phe), CCT (Pro), CTC (Leu), ATC (Ile), TAC (Tyr), AGA (Arg), GCA (Ala) |
| Stickler syndrome type I | COL2A1 | GGT (Gly), CCT (Pro), GGA (Gly), CCC (Pro), GGC (Gly), GAT (Asp), CCA (Pro), GAG (Glu), GAA (Glu), AGA (Arg), CTC (Leu) |
| Supravalvular aortic stenosis | ELN | GGA (Gly), GGT (Gly), GCA (Ala), CCA (Pro), GGG (Gly), CCT (Pro), GTT (Val), CCC (Pro), GTC (Val), GGC (Gly), CTC (Leu), CTT (Leu), GCT (Ala) |
| SYNGAP1-related intellectual disability | SYNGAP1 | CTG (Leu), GAG (Glu), CGG (Arg), CCC (Pro), TCC (Ser), AGC (Ser), AGT (Ser), CCA (Pro), GGT (Gly), TCA (Ser), CTC (Leu), CCT (Pro), TAT (Tyr), CGC (Arg), CTA (Leu) |
| Treacher Collins syndrome | TCOF1 | TCA (Ser), GAG (Glu), AGT (Ser), ACC (Thr), AGC (Ser), GGG (Gly), CCA (Pro), GCA (Ala), CCC (Pro), TCC (Ser), CCT (Pro), AGA (Arg), GCC (Ala), AAG (Lys) |
| Trichorhinophalangeal syndrome type I | TRPS1 | AGT (Ser), TCA (Ser), CAT (His), GAT (Asp), CAA (Gln), ACA (Thr), CTA (Leu), CCA (Pro), GGA (Gly), TCC (Ser), AGA (Arg), CCT (Pro), CCC (Pro), TAT (Tyr), CTC (Leu), CTT (Leu), AAT (Asn), TGT (Cys), GAA (Glu), GCA (Ala) |
| Ulnar-mammary syndrome | TBX3 | TCC (Ser), GCG (Ala), CCG (Pro), CCC (Pro), CTG (Leu), AGC (Ser), ACC (Thr), GCC (Ala), CTC (Leu), TCG (Ser), AGA (Arg), CCT (Pro), GAG (Glu), CGC (Arg) |
| van der Woude syndrome 1 | IRF6 | CCC (Pro), CTG (Leu), GAT (Asp), CCA (Pro), GAG (Glu), TTT (Phe), ACC (Thr), TGG (Trp), AGC (Ser), CAG (Gln), CTC (Leu), CCT (Pro), AGA (Arg), ATC (Ile), GAA (Glu), TAT (Tyr), TAC (Tyr) |

TABLE 2-continued

| Disorder | Gene | Codons |
|---|---|---|
| Waardenburg syndrome type 1 | PAX3 | AGC (Ser), ACC (Thr), CCC (Pro), CTG (Leu), GAG (Glu), AGT (Ser), CCG (Pro), CAA (Gln), CGC (Arg), TCC (Ser), CTC (Leu), CCT (Pro), AGA (Arg), TAC (Tyr), TAT (Tyr) |
| Waardenburg syndrome type 2A | MITF | TCC (Ser), CAT (His), CAA (Gln), CCC (Pro), AGT (Ser), AGC (Ser), GAT (Asp), ACC (Thr), GAA (Glu), GAG (Glu), CTC (Leu), CTT (Leu), AGA (Arg), ATA (Ile), TAT (Tyr), GCA (Ala) |
| Waardenburg syndrome type 4C | SOX10 | CCC (Pro), GAG (Glu), TCA (Ser), CAC (His), AGC (Ser), TCC (Ser), GGC (Gly), CTG (Leu), TCG (Ser), CGC (Arg), CTC (Leu), TAC (Tyr), TAT (Tyr), GCC (Ala), CCA (Pro), GGG (Gly) |

In certain embodiments, the haploinsufficiency disorder is a disorder listed in any one of TABLES 4, 5, 6 or 7 below, together with the haploinsufficient gene associated with each disorder. In certain embodiments, the gene is a gene listed in TABLES 4, 5, 6 or 7, and the first, second, and/or third non-optimal codon is a codon listed in the corresponding row of TABLES 4, 5, 6 or 7. In certain embodiments, the haploinsufficiency disorder is a disorder listed in TABLES 4, 5, 6 or 7, and the first, second, and/or third non-optimal codon is a codon listed in the corresponding row of TABLES 4, 5, 6 or 7. TABLE 4 and TABLE 5 show, respectively, the three and ten least optimal and most overrepresented codons in the indicated genes, as calculated based on percentage codon usage and the tRNA adaptive index (tAI). TABLE 6 and TABLE 7 show, respectively, the three and ten least optimal and most overrepresented codons in the indicated genes, as calculated based on percentage codon usage and a modified tAI value based on a direct quantification of tRNA levels in HEK293 cells rather than estimates of tRNA levels based on tRNA gene copy number.

II. Transfer RNAs that Decode Non-Optimal Codons

A. Transfer RNAs

During protein synthesis, a tRNA delivers an amino acid to a ribosome for insertion into to a growing protein (polypeptide) chain. tRNAs typically are about 70 to 100 nucleotides in length. Active tRNAs contain a 3' CCA sequence that may be transcribed into the tRNA during its synthesis or may be added later during post-transcriptional processing. During aminoacylation, the amino acid that is attached to a given tRNA molecule is covalently attached to the 2' or 3' hydroxyl group of the 3'-terminal ribose to form an aminoacyl-tRNA (aa-tRNA). It is understood that an amino acid can spontaneously migrate from the 2'-hydroxyl group to the 3'-hydroxyl group and vice versa, but it is incorporated into a growing protein chain at the ribosome from the 3'-OH position. A loop at the other end of the folded aa-tRNA molecule contains a sequence of three bases known as the anticodon. When this anticodon sequence hybridizes or base-pairs with a complementary three-base codon sequence in a ribosome-bound mRNA transcript, the aa-tRNA binds to the ribosome and its amino acid is incorporated into the polypeptide chain being synthesized by the ribosome. Since all tRNAs that base-pair with a specific codon are aminoacylated with a single specific amino acid, the translation of the genetic code is effected by tRNAs. Each of the 61 non-termination codons in an mRNA directs the binding of its cognate aa-tRNA and the addition of a single specific amino acid to the growing protein or polypeptide chain being synthesized by the ribosome.

tRNAs are generally highly conserved and are often functional across species. Accordingly, a tRNA derived from a bacterial tRNA, a non-mammalian eukaryotic tRNA, or a mammalian (e.g., human) tRNA may be useful in the practice of the compositions and methods described herein. Nucleotide sequences encoding naturally occurring human tRNAs are known and generally available to those of skill in the art through sources such as Genbank. See also Sprinzl et al. (2005) NUCLEIC ACIDS RES. 33: D139-40; Buckland et al. (1996) GENOMICS 35 (1): 164-71; Schimmel et al. (Eds.) (1979) "Transfer-RNA: Structure, Properties, and Recognition," Cold Spring Harbor Laboratory; Agris (1983) "The Modified Nucleosides of Transfer RNA, II," Alan R. Liss Inc. tRNAs are generally highly conserved and are often functional across species.

In certain embodiments, the tRNA is aminoacylated or is capable of being aminoacylated with any natural amino acid. For example, a tRNA may be capable of being aminoacylated with alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In certain embodiments, the amino acid is selected from serine and arginine.

In certain embodiments, a tRNA comprises the nucleotide sequence of SEQ ID NO: 1, SEQ ID NO: 2 or SEQ ID NO: 3, or a nucleotide sequence having 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, SEQ ID NO: 2, or SEQ ID NO: 3.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87:2264-2268; Altschul, (1993) J. MOL. EVOL. 36, 290-300; Altschul et al., (1997) NUCLEIC ACIDS RES. 25:3389-3402, incorporated by reference) are tailored for sequence similarity searching. For a discussion of basic issues in searching sequence databases see Altschul et al., (1994) NATURE GENETICS 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.,: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

It is contemplated that a tRNA may comprise on or more modifications. Examples of modified tRNAs include: acylated tRNA; alkylated tRNA; a tRNA containing one or more bases other than adenine, cytosine, guanine, or uracil; a tRNA covalently modified by the attachment of a specific ligand or antigenic, fluorescent, affinity, reactive, spectral, or other probe moiety; a tRNA containing one or more ribose moieties that are methylated or otherwise modified; aa-tRNAs that are aminoacylated with an amino acid other than the 20 natural amino acids, including non-natural amino acids that function as a carrier for reagents, specific ligands, or as an antigenic, fluorescent, reactive, affinity, spectral, or other probe; or any combination of these compositions. Examples of modified tRNA molecules are described in Soll et al. (1995) "IRNA: Structure, Biosynthesis, and Function," ASM Press; El Yacoubi et al. (2012) ANNU. REV. GENET. 46:69-95; Grosjean et al. (1998) "Modification and Editing of RNA." ASM Press; Hendrickson et al. (2004) ANNU. REV. BIOCHEM. 73:147-176, 2004; Ibba et al. (2000) ANNU. REV. BIOCHEM. 69:617-650; Johnson et al. (1995) COLD SPRING HARBOR SYMP. QUANT. BIOL. 60:71-82; Johnson et al. (1982) J. MOL. BIOL. 156:113-140; Crowley et al. (1994) CELL 78:61-71; Beier et al. (2001) NUCLEIC ACIDS RES. 29:4767-4782; Torres et al. (2014) TRENDS MOL. MED. 20:306-314; and Bjork et al. (1987) ANNU. REV. BIOCHEM. 56:263-287.

Figure 2A:
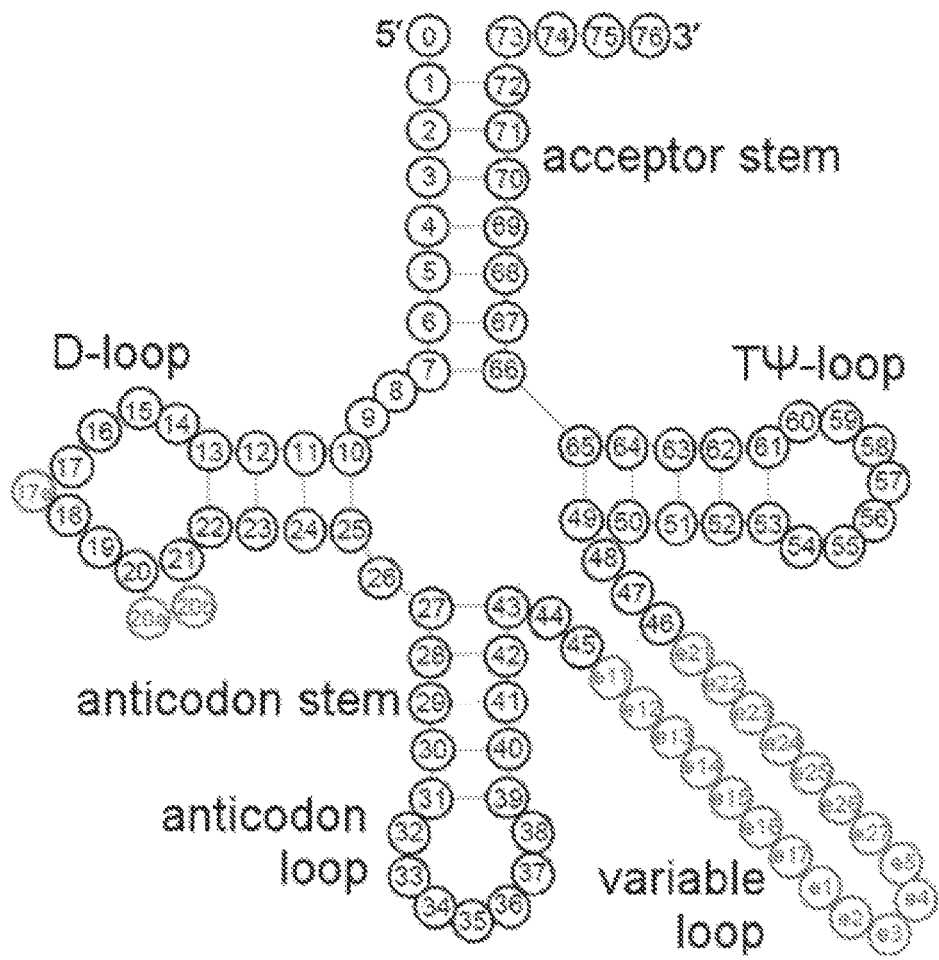
FIG. 2A is a consensus tRNA secondary structure. The numbering of the residues is based on the tRNA numbering system described in Steinberg et al. (1993) NUCLEIC ACIDS RES. 21:3011-15.

In certain embodiments, a tRNA comprises a naturally occurring nucleotide modification. Naturally occurring tRNAs contain a wide variety of post-transcriptionally modified nucleotides, which are described, for example, in Machnicka et al. (2014) RNA BIOLOGY 11 (12): 1619-1629, and include one or more of the residues as shown in FIG. 2B. In certain embodiments, the tRNA comprises one or more of the residues selected from the group consisting of: 2'-O-methylguanosine or G at position 0; pseudouridine or U at position 1; 2'-O-methyladenosine, A, 2'-O-methyluridine, U, 2'-O-methylcytidine, C, 2'-O-methylguanosine, or G at position 4; N2-methylguanosine or G at position 6; N2-methylguanosine or G at position 7; 1-methyladenosine, A, 1-methylguanosine, G, or a modified G at position 9; N2-methylguanosine or G at position 10; N4-acetylcytidine or C at position 12; pseudouridine, U, 2'-O-methylcytidine, or C at position 13; 1-methyladenosine, A, or a modified A at position 14; dihydrouridine (D) or U at position 16; D or U at position 17; 2'-O-methylguanosine or G at position 18; 3-(3-amino-3-carboxypropyl) uridine, D, or U at position 20; 3-(3-amino-3-carboxypropyl) uridine, D, pseudouridine, U, or a modified U at position 20a; D, pseudouridine, or U at position 20b; pseudouridine or U at position 25; pseudouridine, U, N2,N2-dimethylguanosine, N2-methylguanosine, G, or a modified G at position 26; pseudouridine, U, N2,N2-dimethylguanosine, or G at position 27; pseudouridine or U at position 28; pseudouridine or U at position 30; pseudouridine or U at position 31; 2'-O-methylpseudouridine, 2'-O-methyluridine, pseudouridine, U, 2'-O-methylcytidine, 3-methylcytidine, C, or a modified C at position 32; inosine, A, 2-thiouridine, 2'-O-methyluridine, 5-(carboxyhydroxymethyl) uridine methyl ester, 5-carbamoylmethyluridine, 5-carboxymethylaminomethyl-2'-O-methyluridine, 5-methoxycarbonylmethyl-2-thiouridine, 5-methoxycarbonylmethyluridine, pseudouridine, U, a modified U, 2'-O-methylcytidine, 5-formyl-2'-O-methylcytidine, 5-methylcytidine, C, a modified C, queuosine, mannosyl-queuosine, galactosyl-queuosine, 2'-O-methylguanosine, or G at position 34; pseudouridine or U at position 35; pseudouridine, U, or a modified U at position 36; 1-methylinosine, 2-methylthio-N6-threonylcarbamoyladenosine, N6-isopentenyladenosine, N6-methyl-N6-threonylcarbamoyladenosine, N6-threonylcarbamoyladenosine, A, a modified A, 1-methylguanosine, peroxywybutosine, wybutosine, G, or a modified G at position 37; pseudouridine, U, 5-methylcytidine, C, or a modified C at position 38; 1-methylpseudouridine, 2'-O-methylpseudouridine, 2'-O-methyluridine, pseudouridine, U, 2'-O-methylguanosine, or G at position 39; pseudouridine, U, 5-methylcytidine, or C at position 40; 2'-O-methyluridine, U, or a modified U at position 44; pseudouridine or U at position e11; pseudouridine or U at position e12; pseudouridine or U at position e14; 3-methylcytidine or C at position e2; 7-methylguanosine or G at position 46; D, U, or a modified U at position 47; D, U, 5-methylcytidine, C, or a modified C at position 48; A, a modified A, 5-methylcytidine, C, or a modified C at position 49; pseudouridine, U, 5-methylcytidine, or C at position 50; 5,2'-O-dimethyluridine, 5-methyluridine, pseudouridine, or U at position 54; pseudouridine or U at position 55; 1-methyladenosine, A, or a modified A at position 58; 2'-O-ribosyladenosine (phosphate), A, 2'-O-ribosylguanosine (phosphate), G, or a modified G at position 64; pseudouridine or U at position 65; pseudouridine, U, N2-methylguanosine, or G at position 67; pseudouridine or U at position 68; and, pseudouridine, U, 5-methylcytidine, or C at position 72. The numbering of the residues is based on the tRNA numbering system described in Steinberg et al., (1993) NUCLEIC ACIDS RES. 21:3011-15.

In certain embodiments, the tRNA comprises one or more nucleotide modifications selected from 5-methyl uridine, pseudouridine, dihydrouridine, and 1-methyladenosine.

B. Non-Optimal Codons tRNAs useful in the compositions and methods described herein comprise an anticodon that hybridizes to a non-optimal codon.

Protein synthesis is directed by a genetic code that includes 61 three-base-pair codons that code for amino acids that are incorporated into the protein being synthesized and 3 three-base-pair codons (referred to as stop or termination codons) that terminate the synthesis of a protein. The degeneracy of the genetic code is a mathematical consequence based on the 61 three-base-pair codon combinations that code for 20 amino acids. Synonymous codons refer to three-base pair codons that code for the same amino acid. It has been generally believed that synonymous codon substitutions are silent, and have no impact on gene expression or the amount of resulting functional gene product. However, it appears that synonymous codons are differentially recognized by the translational apparatus. This concept is referred to as codon optimality. Conceptually, codon optimality reflects the balance between the supply of aminoacylated tRNA molecules and their demand imposed by the concentration of codons engaged in translation. Thus, the ribosome decodes some codons quickly because their cognate tRNAs are relatively more abundant, whereas other codons are read more slowly because their tRNA concentrations are relatively less abundant (Tuller et al. (2010) CELL 141 (2): 344-54; Novoa et al. (2012) TRENDS GENET. 28 (11): 574-81). In addition, codon optimality is based somewhat on the accuracy of tRNA anticodon/codon interactions, which can influence decoding rate (Akashi (1994) GENETICS 136 (3): 927-35; Drummond et al. (2008) CELL 134 (2): 341-52).

Optimality of codons within an mRNA transcript has been shown to influence the stability of the mRNA transcript, and the rate at which the mRNA transcript is translated by the ribosome (Presnyak et al. (2015) CELL 160 (6): 1111-24; Radhakrishnan et al. (2016) CELL 167 (1): 122-132). Accordingly, as used herein, the term "non-optimal codon" refers to a codon in an mRNA transcript that is recognized by a tRNA that is less abundant in the cell than a different tRNA that recognizes another codon for the same amino acid. Often, the substitution of a non-optimal codon with a different codon that encodes for the same amino acid (i.e., a synonymous codon), but that is read by a tRNA that is more abundant in the cell, increases the stability of the mRNA transcript, and/or the rate at which the mRNA transcript is translated by the ribosome. As a result, a non-optimal codon is any codon whose overexpression of its cognate tRNA enhances mRNA stability, abundance, and or translational elongation.

Codon-optimality can be measured or quantified by one or more of the following approaches, including the tRNA adaptation index (tAI), normalized translational efficiency (nTE), species specific tRNA adaptation index (sTAI), codon adaptation index (CAI), gCAI, and codon occurrence to mRNA stability correlation coefficient (CSC).

tAI is an estimate of codon optimality for each codon that takes into account estimates of cellular concentration of tRNA (based on tRNA gene copy numbers) and efficiencies of decoding. tAI is described, for example, in dos Reis et al. (2004) NUCLEIC ACIDS RES. 32 (17): 5036-5044, and Mahlab et al. (2014) PLOS COMPUT. BIOL. 10 (1): e1003294. In certain embodiments, a non-optimal codon has a tAI value less than the median tAI value of all the codons for a given species, e.g., humans.

In certain embodiments, a non-optimal codon has a value of 0.47 or lower, as determined by the tAI. For example, in certain embodiments, a non-optimal codon is selected from CTA (Leu), TCA (Ser), CAT (His), AGT (Ser), TTA (Leu), GTA (Val), ATA (Ile), CGC (Arg), TCG (Ser), TTT (Phe), AGA (Arg), CGA (Arg), ACA (Thr), CCG (Pro), GGT (Gly), AGG (Arg), CGG (Arg), CAA (Gln), CGT (Arg), GAT (Asp), TAT (Tyr), ACC (Thr), TCC (Ser), ACG (Thr), CCC (Pro), CTC (Leu), GTC (Val), TGG (Trp), CCA (Pro), GCG (Ala), TTG (Leu), AGC (Ser), GGA (Gly), CTG (Leu), ACT (Thr), CAC (His), TCT (Ser), GCA (Ala), CCT (Pro), CTT (Leu), GTT (Val), GGG (Gly), GAA (Glu), TTC (Phe), GAG (Glu), TGT (Cys), TAC (Tyr), GGC (Gly), AAT (Asn), GAC (Asp), and any combination thereof.

In certain embodiments, a non-optimal codon has a value of 0.25 or lower, as determined by the tAI. For example, in certain embodiments, a non-optimal codon is selected from CTA (Leu), TCA (Ser), CAT (His), AGT (Ser), TTA (Leu), GTA (Val), ATA (Ile), CGC (Arg), TCG (Ser), TTT (Phe), AGA (Arg), CGA (Arg), ACA (Thr), CCG (Pro), GGT (Gly), AGG (Arg), CGG (Arg), CAA (Gln), CGT (Arg), GAT (Asp), TAT (Tyr), ACC (Thr), TCC (Ser), ACG (Thr), CCC (Pro), CTC (Leu), GTC (Val), TGG (Trp), CCA (Pro), GCG (Ala), TTG (Leu), AGC (Ser), and any combination thereof.

In certain embodiments, a non-optimal codon is selected from CTA (Leu), TCA (Ser), CAT (His), AGT (Ser), TTA (Leu), GTA (Val), ATA (Ile), CGC (Arg), TCG (Ser), TTT (Phe), AGA (Arg), CGA (Arg), ACA (Thr), CCG (Pro), GGT (Gly), AGG (Arg), CGG (Arg), CAA (Gln), CGT (Arg), GAT (Asp), and any combination thereof. In certain embodiments, a non-optimal codon is selected from CTA (Leu), TCA (Ser), CAT (His), AGT (Ser), TTA (Leu), GTA (Val), ATA (Ile), CGC (Arg), TCG (Ser), TTT (Phe), and any combination thereof. In certain embodiments, a non-optimal codon is selected from CTA (Leu), TCA (Ser), CAT (His), AGT (Ser), TTA (Leu), and any combination thereof.

Codon optimality may also be measured by a modified version of tAI that is based on a direct quantification of tRNA levels in a given cell in place of estimates based on tRNA gene copy number. tRNA levels may be determined by any method known in the art, for example, as described in Zheng et al. (2015) NAT. METHODS. 12 (9): 835-837. For example, in certain embodiments, a non-optimal codon is selected from AGA (Arg), CTC (Leu), ATA (Ile), CCC (Pro), CTA (Leu), CTT (Leu), TAT (Tyr), CCT (Pro), TGT (Cys), CGC (Arg), GCA (Ala), TCC (Ser), TAC (Tyr), GCG (Ala), AGG (Arg), CGT (Arg), CCG (Pro), GGA (Gly), CCA (Pro), TGC (Cys), TCT (Ser), TCG (Ser), TTG (Leu), AGT (Ser), TTT (Phe), ACG (Thr), AAT (Asn), ACA (Thr), GAA (Glu), ATC (Ile), TGG (Trp), and any combination thereof. In certain embodiments, a non-optimal codon is selected from AGA (Arg), CTC (Leu), ATA (Ile), CCC (Pro), CTA (Leu), CTT (Leu), TAT (Tyr), CCT (Pro), TGT (Cys), CGC (Arg), GCA (Ala), TCC (Ser), TAC (Tyr), GCG (Ala), AGG (Arg), CGT (Arg), CCG (Pro), GGA (Gly), CCA (Pro), TGC (Cys), and any combination thereof. In certain embodiments, a non-optimal codon is selected from AGA (Arg), CTC (Leu), ATA (Ile), CCC (Pro), CTA (Leu), CTT (Leu), TAT (Tyr), CCT (Pro), TGT (Cys), CGC (Arg), and any combination thereof. In certain embodiments, a non-optimal codon is selected from AGA (Arg), CTC (Leu), ATA (Ile), CCC (Pro), CTA (Leu), and any combination thereof.

In certain embodiments, the average tAI value of the codons in the gene is between about 0.15 and about 0.5, about 0.15 and about 0.45, about 0.15 and about 0.4, about 0.15 and about 0.35, about 0.15 and about 0.3, about 0.15 and about 0.25, about 0.15 and about 0.2, about 0.2 and about 0.5, about 0.2 and about 0.45, about 0.2 and about 0.4, about 0.2 and about 0.35, about 0.2 and about 0.3, about 0.2 and about 0.25, about 0.25 and about 0.5, about 0.25 and about 0.45, about 0.25 and about 0.4, about 0.25 and about 0.35, about 0.25 and about 0.3, about 0.3 and about 0.5, about 0.3 and about 0.45, about 0.3 and about 0.4, about 0.3 and about 0.35, about 0.35 and about 0.5, about 0.35 and about 0.45, about 0.35 and about 0.4, about 0.4 and about 0.5, about 0.4 and about 0.45, and about 0.45 and about 0.5.

In certain embodiments, the average tAI value of the codons in the gene is less than about 0.15, about 0.2, about 0.25, about 0.3, about 0.35, about 0.4, about 0.45, or about 0.5.

stAI is an estimate of codon optimality for each codon that takes into account estimates of cellular concentration of tRNA and efficiencies of decoding, and weights decoding efficiency in a species-specific manner. stAI is described, for example, in Sabi et al. (2014) DNA RES. 21 (5): 511-525. In certain embodiments, a non-optimal codon has a stAI value less than the median stAI value of all the codons for a given species, e.g., humans.

nTE is an estimate of codon optimality for each codon that takes into account estimates of cellular concentration of tRNA, efficiencies of decoding, and usage of codons in the cellular mRNA pool. nTE is described, for example, in Pechman et al. (2013) NAT. STRUCT. MOL. BIOL. 20 (2): 237-43. In certain embodiments, a non-optimal codon has an nTE value less than the median nTE value of all the codons for a given species, e.g., humans.

CAI estimates codon optimality by scoring codon frequency in highly expressed genes. Accordingly, codon optimality as estimated by CAI can change depending upon the gene set designated as highly expressed. CAI is described, for example, in Sharp et al. (1987) NUCLEIC ACIDS RES. 15 (3): 1281-95. gCAI is similar to CAI, but uses the entire expressed transcriptome of a given cell. In certain embodiments, a non-optimal codon has a CAI value less than the median CAI value of all the codons for a given species, e.g., humans.

CSC estimates codon optimality by correlating codon occurrence with mRNA half-life measurements. CSC is described, for example, in Presnyak et al. (2015) CELL 160 (6): 1111-24. In certain embodiments, a non-optimal codon has a CSC value less than the median CSC value of all the codons for a given species, e.g., humans. In certain embodiments, a non-optimal codon has a value of 0 or lower, as determined by the CSC.

In certain embodiments, a non-optimal codon is selected from ATA, GTA, and AGA, and any combination thereof. In certain embodiments, the non-optimal codon is ATA. In certain embodiments, the non-optimal codon is GTA. In certain embodiments, the non-optimal codon is AGA. In certain embodiments, the non-optimal codons are ATA and GTA. In certain embodiments, the non-optimal codons are ATA and AGA. In certain embodiments, the non-optimal codons are GTA and AGA. In certain embodiments, the non-optimal codons are ATA, GTA, and AGA.

In certain embodiments, about 20% to about 70%, about 20% to about 60%, about 20% to about 50%, about 20% to about 40%, about 20% to about 30%, about 30% to about 70%, about 30% to about 60%, about 30% to about 50%, about 30% to about 40%, about 40% to about 70%, about 40% to about 60%, about 40% to about 50%, about 50% to about 70%, about 50% to about 60%, or about 60% to about 70% of the codons in the gene are non-optimal codons. In certain embodiments, greater than about 20%, about 30%, about 40%, about 50%, about 60%, or about 70% of the codons in the gene are non-optimal codons. In certain embodiments greater than about 40% or about 50% of the codons in the gene are non-optimal codons.

III. Methods of Making Transfer RNAs

It is contemplated the tRNA molecules useful in the practice of the compositions and methods described herein can be produced by methods known in the art, including extracellular production by synthetic chemical methods, intracellular production by recombinant DNA methods, or purification from natural sources.

For example, DNA molecules encoding tRNAs can be synthesized chemically or by recombinant DNA methodologies. For example, the sequences of the tRNAs can be synthesized or cloned from libraries by conventional hybridization techniques or polymerase chain reaction (PCR) techniques, using the appropriate synthetic nucleic acid primers. The resulting DNA molecules encoding the tRNAs can be ligated to other appropriate nucleotide sequences, including, for example, expression control sequences to produce conventional gene expression constructs (i.e., expression vectors) encoding the tRNAs. Production of defined gene constructs is within routine skill in the art. Nucleic acids encoding desired tRNAs can be incorporated (ligated) into expression vectors, such as the expression vectors described in the following section, which can be introduced into host cells through conventional transfection or transformation techniques. Examples of host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the tRNAs. Specific expression and purification conditions will vary depending upon the expression system employed.

Alternatively, tRNAs can be chemically synthesized or purified from natural sources by methods known in art. When a tRNA is aminoacylated prior to introduction into the cell or administration to the subject, the tRNA may be aminoacylated with a desired amino acid by any method known in the art, including chemical or enzymatic aminoacylation.

IV. Expression Vectors

The tRNAs of interest may be expressed in a cell of interest by incorporating a gene encoding a tRNA of interest into an expression vector. As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

In certain embodiments, the expression vector is a viral vector. The term "virus" is used herein to refer any of the obligate intracellular parasites having no protein-synthesizing or energy-generating mechanism. Examples of viral vectors include retroviral vectors (e.g., lentiviral vectors), adenoviral vectors, adeno-associated viral vectors, herpesviruses vectors, epstein-barr virus (EBV) vectors, polyomavirus vectors (e.g., simian vacuolating virus 40 (SV40) vectors), poxvirus vectors, and pseudotype virus vectors.

The virus may be a RNA virus (having a genome that is composed of RNA) or a DNA virus (having a genome composed of DNA). In certain embodiments, the viral vector is a DNA virus vector. Exemplary DNA viruses include parvoviruses (e.g., adeno-associated viruses), adenoviruses, asfarviruses, herpesviruses (e.g., herpes simplex virus 1 and 2 (HSV-1 and HSV-2), epstein-barr virus (EBV), cytomegalovirus (CMV)), papillomoviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). In certain embodiments, the viral vector is a RNA virus vector. Examples of RNA viruses include bunyaviruses (e.g., hantavirus), coronaviruses, ebolaviruses, flaviviruses (e.g., yellow fever virus, west nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, noroviruses (e.g., Norwalk virus), poliovirus, respiratory syncytial virus (RSV), retroviruses (e.g., human immunodeficiency virus-1 (HIV-1)) and toroviruses.

In certain embodiments, the expression vector comprises a regulatory sequence or promoter operably linked to the nucleotide sequence encoding the tRNA. The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

tRNA genes preferably have strong promoters that are active in a variety of cell types. The promoters for eukaryotic tRNA genes typically are present within the structural sequences encoding the tRNA molecule itself. Although there are elements, which regulate transcriptional activity within the 5' upstream region, the length of an active transcriptional unit may be considerably less than 500 base pairs.

Additional examples of promoters which may be employed include, but are not limited to, the retroviral LTR, the SV40 promoter, the human cytomegalovirus (CMV) promoter, the U6 promoter, or any other promoter (e.g., cellular promoters such as eukaryotic cellular promoters including, but not limited to, the histone, pol III, and β-actin promoters). Other viral promoters, which can be employed include, but are not limited to, adenovirus promoters, TK promoters, and B19 parvovirus promoters. The selection of a promoter will be apparent to those skilled in the art from the teachings contained herein.

In certain embodiments, an expression vector comprises a tRNA coding sequence comprising the nucleotide sequence of SEQ ID NO: 1, SEQ ID NO: 2, and/or SEQ ID NO: 3, or a nucleotide sequence having 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, SEQ ID NO: 2, and/or SEQ ID NO: 3.

In certain embodiments, in addition to a tRNA coding sequence, the expression vector comprises a nucleotide sequence corresponding to the genomic DNA sequence flanking a corresponding wild-type tRNA gene. For example, in certain embodiments, an expression vector comprises the nucleotide sequence of SEQ ID NO: 4, SEQ ID NO: 5, SEQ ID NO: 6, SEQ ID NO: 7, SEQ ID NO: 8, or SEQ ID NO: 9, or a nucleotide sequence having 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 4, SEQ ID NO: 5, SEQ ID NO: 6, SEQ ID NO: 7, SEQ ID NO: 8, or SEQ ID NO: 9.

Adeno-Associated Virus (AAV) Vectors

In certain embodiments, an expression vector is an adeno-associated virus (AAV) vector. AAV is a small, nonenveloped icosahedral virus of the genus Dependoparvovirus and family Parvovirus. AAV has a single-stranded linear DNA genome of approximately 4.7 kb. AAV is capable of infecting both dividing and quiescent cells of several tissue types, with different AAV serotypes exhibiting different tissue tropism.

AAV includes numerous serologically distinguishable types including serotypes AAV-1 to AAV-12, as well as more than 100 serotypes from nonhuman primates (See, e.g., Srivastava (2008) J. CELL BIOCHEM., 105 (1): 17-24, and Gao et al. (2004) J. VIROL., 78 (12), 6381-6388). The serotype of the AAV vector used in the compositions and methods described herein can be selected by a skilled person in the art based on the efficiency of delivery, tissue tropism, and immunogenicity. For example, AAV-1, AAV-2, AAV-4, AAV-5, AAV-8, and AAV-9 can be used for delivery to the central nervous system; AAV-1, AAV-8, and AAV-9 can be used for delivery to the heart; AAV-2 can be used for delivery to the kidney; AAV-7, AAV-8, and AAV-9 can be used for delivery to the liver; AAV-4, AAV-5, AAV-6, AAV-9 can be used for delivery to the lung, AAV-8 can be used for delivery to the pancreas, AAV-2, AAV-5, and AAV-8 can be used for delivery to the photoreceptor cells; AAV-1, AAV-2, AAV-4, AAV-5, and AAV-8 can be used for delivery to the retinal pigment epithelium; AAV-1, AAV-6, AAV-7, AAV-8, and AAV-9 can be used for delivery to the skeletal muscle. In certain embodiments, the AAV capsid protein comprises a sequence as disclosed in U.S. Pat. No. 7,198,951, such as, but not limited to, AAV-9 (SEQ ID NOs: 1-3 of U.S. Pat. No. 7,198,951), AAV-2 (SEQ ID NO: 4 of U.S. Pat. No. 7,198,951), AAV-1 (SEQ ID NO: 5 of U.S. Pat. No. 7,198,951), AAV-3 (SEQ ID NO: 6 of U.S. Pat. No. 7,198,951), and AAV-8 (SEQ ID NO: 7 of U.S. Pat. No. 7,198,951). AAV serotypes identified from rhesus monkeys, e.g., rh.8, rh.10, rh.39, rh.43, and rh.74, are also contemplated. Besides the natural AAV serotypes, modified AAV capsids have been developed for improving efficiency of delivery, tissue tropism, and immunogenicity. Examples of natural and modified AAV capsids are disclosed in U.S. Pat. Nos. 7,906,111, 9,493,788, and 7,198,951, and PCT Publication No. WO2017189964A2.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous gene of interest. Accordingly, in certain embodiments, the AAV vector comprises a genome comprising an expression cassette for an exogenous gene flanked by a 5' ITR and a 3' ITR. The ITRs may be derived from the same serotype as the capsid or a derivative thereof. Alternatively, the ITRs may be of a different serotype from the capsid, thereby generating a pseudotyped AAV. In certain embodiments, the ITRs are derived from AAV-2. In certain embodiments, the ITRs are derived from AAV-5. At least one of the ITRs may be modified to mutate or delete the terminal resolution site, thereby allowing production of a self-complementary AAV vector.

The rep and cap proteins can be provided in trans, for example, on a plasmid, to produce an AAV vector. A host cell line permissive of AAV replication must express the rep and cap genes, the ITR-flanked expression cassette, and helper functions provided by a helper virus, for example adenoviral genes E1a, E1b55K, E2a, E4orf6, and VA (Weitzman et al., Adeno-associated virus biology. Adeno-Associated Virus: Methods and Protocols, pp. 1-23, 2011). Methods for generating and purifying AAV vectors have been described in detail (See e.g., Mueller et al., (2012) CURRENT PROTOCOLS IN MICROBIOLOGY, 14D.1.1-14D.1.21, Production and Discovery of Novel Recombinant Adeno-Associated Viral Vectors). Numerous cell types are suitable for producing AAV vectors, including HEK293 cells, COS cells, HeLa cells, BHK cells, Vero cells, as well as insect cells (See e.g. U.S. Pat. Nos. 6,156,303, 5,387,484, 5,741,683, 5,691,176, 5,688,676, and 8,163,543, U.S. Patent Publication No. 20020081721, and PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the compositions and methods described herein. Similarly, it is contemplated that any adenoviral type may be used, and a person of skill in the art will be able to identify AAV and adenoviral types suitable for the production of their desired recombinant AAV vector (rAAV). AAV particles may be purified, for example, by affinity chromatography, iodixonal gradient, or CsCl gradient.

AAV vectors may have single-stranded genomes that are 4.7 kb in size, or are larger or smaller than 4.7 kb, including oversized genomes that are as large as 5.2 kb, or as small as 3.0 kb. Thus, where the exogenous gene of interest to be expressed from the AAV vector is small, the AAV genome may comprise a stuffer sequence. Further, vector genomes may be substantially self-complementary thereby allowing for rapid expression in the cell. In certain embodiments, the genome of a self-complementary AAV vector comprises from 5' to 3': a 5' ITR; a first nucleic acid sequence comprising a promoter and/or enhancer operably linked to a coding sequence of a gene of interest; a modified ITR that does not have a functional terminal resolution site; a second nucleic acid sequence complementary or substantially complementary to the first nucleic acid sequence; and a 3' ITR. AAV vectors containing genomes of all types are suitable for use in methods described herein.

Non-limiting examples of AAV vectors include pAAV-MCS (Agilent Technologies), pAAVK-EF1α-MCS (System Bio Catalog #AAV502A-1), pAAVK-EF1α-MCS1-CMV-MCS2 (System Bio Catalog #AAV503A-1), pAAV-Zs-Green1 (Clontech Catalog #6231), pAAV-MCS2 (Addgene Plasmid #46954), AAV-Stuffer (Addgene Plasmid #106248), pAAVscCBPIGpluc (Addgene Plasmid #35645), AAVS1_Puro_PGK1_3×FLAG_Twin_Strep (Addgene Plasmid #68375), pAAV-RAM-d2TTA::TRE-MCS-WPRE-pA (Addgene Plasmid #63931), pAAV-UbC (Addgene Plasmid #62806), pAAVS1-P-MCS (Addgene Plasmid #80488), pAAV-Gateway (Addgene Plasmid #32671), pAAV-Puro_siKD (Addgene Plasmid #86695), pAAVS1-Nst-MCS (Addgene Plasmid #80487), pAAVS1-Nst-CAG-DEST (Addgene Plasmid #80489), pAAVS1-P-CAG-DEST (Addgene Plasmid #80490), pAAVf-EnhCB-lacZnls (Addgene Plasmid #35642), and pAAVS1-shRNA (Addgene Plasmid #82697). These vectors can be modified to be suitable for therapeutic use. For example, an exogenous gene of interest can be inserted in a multiple cloning site, and a selection marker (e.g., puro or a gene encoding a fluorescent protein) can be deleted or replaced with another (same or different) exogenous gene of interest. Further examples of AAV vectors are disclosed in U.S. Pat. Nos. 5,871,982, 6,270,996, 7,238,526, 6,943,019, 6,953,690, 9,150,882, and 8,298,818, U.S. Patent Publication No. 2009/0087413, and PCT Publication Nos. WO2017075335A1, WO2017075338A2, and WO2017201258A1.

In certain embodiments, the expression vector is an AAV vector capable of targeting the nervous system, e.g., the central nervous system, in a subject, e.g., a human subject. Exemplary AAV vectors that can target the nervous system include the AAV9 variants AAV-PHP.B (See, e.g., Deverman et al. (2016) NAT. BIOTECHNOL. 34 (2): 204-209), AAV-AS (See, e.g., Choudhury et al. (2016) MOL. THER. 24:726-35), and AAV-PHP.eB (See, e.g., Chan et al. (2017) NAT. NEUROSCI. 20:1172-79). Additional exemplary AAV-based strategies for targeting the nervous system are described in Bedrook et al. (2018) ANNU REV NEUROSCI. 41:323-348.

Lentivirus Vectors

In certain embodiments, the viral vector can be a retroviral vector. Examples of retroviral vectors include moloney murine leukemia virus vectors, spleen necrosis virus vectors, and vectors derived from retroviruses such as rous sarcoma virus, harvey sarcoma virus, avian leukosis virus, human immunodeficiency virus, myeloproliferative sarcoma virus, and mammary tumor virus. Retroviral vectors are useful as agents to mediate retroviral-mediated gene transfer into eukaryotic cells.

In certain embodiments, the retroviral vector is a lentiviral vector. Examples of lentiviral vectors include vectors derived from human immunodeficiency virus-1 (HIV-1), human immunodeficiency virus-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), and caprine arthritis encephalitis virus (CAEV).

Retroviral vectors typically are constructed such that the majority of sequences coding for the structural genes of the virus are deleted and replaced by the gene(s) of interest. More often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal. Accordingly, a minimum retroviral vector comprises from 5' to 3': a 5' long terminal repeat (LTR), a packaging signal, an optional exogenous promoter and/or enhancer, an exogenous gene of interest, and a 3' LTR. If no exogenous promoter is provided, gene expression is driven by the 5' LTR, which is a weak promoter and requires the presence of Tat to activate expression. The structural genes can be provided in separate vectors for manufacture of the lentivirus, rendering the produced virions replication-defective. Specifically, with respect to lentivirus, the packaging system may comprise a single packaging vector encoding the Gag, Pol, Rev, and Tat genes, and a third, separate vector encoding the envelope protein Env (usually VSV-G due to its wide infectivity). To improve the safety of the packaging system, the packaging vector can be split, expressing Rev from one vector, Gag and Pol from another vector. Tat can also be eliminated from the packaging system by using a retroviral vector comprising a chimeric 5' LTR, wherein the U3 region of the 5' LTR is replaced with a heterologous regulatory element.

These new genes can be incorporated into the proviral backbone in several general ways. The most straightforward constructions are ones in which the structural genes of the retrovirus are replaced by a single gene which then is transcribed under the control of the viral regulatory sequences within the LTR. Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Accordingly, the new gene(s) are flanked by 5' and 3' LTRs, which serve to promote transcription and polyadenylation of the virion RNAs, respectively. The term "long terminal repeat" or "LTR" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals, and sequences needed for replication and integration of the viral genome. The U3 region contains the enhancer and promoter elements. The U5 region is the sequence between the primer binding site and the R region and contains the polyadenylation sequence. The R (repeat) region is flanked by the U3 and U5 regions. In certain embodiments, the R region comprises a trans-activation response (TAR) genetic element, which interacts with the trans-activator (tat) genetic element to enhance viral replication. This element is not required in embodiments wherein the U3 region of the 5' LTR is replaced by a heterologous promoter.

In certain embodiments, the retroviral vector comprises a modified 5' LTR and/or 3' LTR. Modifications of the 3' LTR are often made to improve the safety of lentiviral or retroviral systems by rendering viruses replication-defective. In specific embodiments, the retroviral vector is a self-inactivating (SIN) vector. As used herein, a SIN retroviral vector refers to a replication-defective retroviral vector in which the 3' LTR U3 region has been modified (e.g., by deletion or substitution) to prevent viral transcription beyond the first round of viral replication. This is because the 3' LTR U3 region is used as a template for the 5' LTR U3 region during viral replication and, thus, the viral transcript cannot be made without the U3 enhancer-promoter. In a further embodiment, the 3' LTR is modified such that the U5 region is replaced, for example, with an ideal polyadenylation sequence. It should be noted that modifications to the LTRs such as modifications to the 3' LTR, the 5' LTR, or both 3' and 5' LTRs, are also described herein.

In certain embodiments, the U3 region of the 5' LTR is replaced with a heterologous promoter to drive transcription of the viral genome during production of viral particles. Examples of heterologous promoters, which can be used, include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus, because there is no complete U3 sequence in the virus production system.

Adjacent to the 5' LTR are sequences necessary for reverse transcription of the genome (the tRNA primer binding site) and for efficient packaging of viral RNA into particles (the Psi site). As used herein, the term "packaging signal" or "packaging sequence" refers to sequences located within the retroviral genome which are required for encapsidation of retroviral RNA strands during viral particle formation (see e.g., Clever et al., 1995 J. VIROLOGY, 69 (4): 2101-09). The packaging signal may be a minimal packaging signal (also referred to as the psi [ψ] sequence) needed for encapsidation of the viral genome.

In certain embodiments, the retroviral vector (e.g., lentiviral vector) further comprises a FLAP. As used herein, the term "FLAP" refers to a nucleic acid whose sequence includes the central polypurine tract and central termination sequences (cPPT and CTS) of a retrovirus, e.g., HIV-1 or HIV-2. Examples of FLAP elements are described in U.S. Pat. No. 6,682,907 and in Zennou et al. (2000) CELL 101:173. During reverse transcription, central initiation of the plus-strand DNA at the cPPT and central termination at the CTS lead to the formation of a three-stranded DNA structure: a central DNA flap. While not wishing to be bound by any theory, the DNA flap may act as a cis-active determinant of lentiviral genome nuclear import and/or may increase the titer of the virus. In particular embodiments, the retroviral vector backbones comprise one or more FLAP elements upstream or downstream of the heterologous genes of interest in the vectors. For example, in particular embodiments, a transfer plasmid includes a FLAP element. In one embodiment, a vector described herein comprises a FLAP element isolated from HIV-1.

In certain embodiments, the retroviral vector (e.g., lentiviral vector) further comprises an export element. In one embodiment, retroviral vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) RRE (see e.g., Cullen et al., (1991) J. VIROL. 65:1053; and Cullen et al., (1991) CELL 58:423) and the hepatitis B virus post-transcriptional regulatory element (HPRE). Generally, the RNA export element is placed within the 3' UTR of a gene, and can be inserted as one or multiple copies.

In certain embodiments, the retroviral vector (e.g., lentiviral vector) further comprises a posttranscriptional regulatory element. A variety of posttranscriptional regulatory elements can increase expression of a heterologous nucleic acid, e.g., woodchuck hepatitis virus posttranscriptional regulatory element (WPRE; see Zufferey et al., (1999) J. VIROL., 73:2886); the posttranscriptional regulatory element present in hepatitis B virus (HPRE) (Huang et al., MOL. CELL. BIOL., 5:3864); and the like (Liu et al., (1995), GENES DEV., 9:1766). The posttranscriptional regulatory element is generally positioned at the 3' end the heterologous nucleic acid sequence. This configuration results in synthesis of an mRNA transcript whose 5' portion comprises the heterologous nucleic acid coding sequences and whose 3' portion comprises the posttranscriptional regulatory element sequence. In certain embodiments, vectors described herein lack or do not comprise a posttranscriptional regulatory element, such as a WPRE or HPRE, because in some instances these elements increase the risk of cellular transformation and/or do not substantially or significantly increase the amount of mRNA transcript or increase mRNA stability. Therefore, in certain embodiments, vectors described herein lack or do not comprise a WPRE or HPRE as an added safety measure.

Elements directing the efficient termination and polyadenylation of the heterologous nucleic acid transcripts increase heterologous gene expression. Transcription termination signals are generally found downstream of the polyadenylation signal. Accordingly, in certain embodiments, the retroviral vector (e.g., lentiviral vector) further comprises a polyadenylation signal. The term "polyadenylation signal" or "polyadenylation sequence" as used herein denotes a DNA sequence, which directs both the termination and polyadenylation of the nascent RNA transcript by RNA polymerase H. Efficient polyadenylation of the recombinant transcript is desirable as transcripts lacking a polyadenylation signal are unstable and are rapidly degraded. Illustrative examples of polyadenylation signals that can be used in a vector described herein, includes an ideal polyadenylation sequence (e.g., AATAAA, ATTAAA AGTAAA), a bovine growth hormone polyadenylation sequence (BGHpA), a rabbit β-globin polyadenylation sequence (rβgpA), or another suitable heterologous or endogenous polyadenylation sequence known in the art.

In certain embodiments, a retroviral vector further comprises an insulator element. Insulator elements may contribute to protecting retrovirus-expressed sequences, e.g., therapeutic genes, from integration site effects, which may be mediated by cis-acting elements present in genomic DNA and lead to deregulated expression of transferred sequences (i.e., position effect; see, e.g., Burgess-Beusse et al., (2002) PROC. NATL. ACAD. SCI., USA, 99:16433; and Zhan et al., 2001, HUM. GENET., 109:471). In certain embodiments, the retroviral vector comprises an insulator element in one or both LTRs or elsewhere in the region of the vector that integrates into the cellular genome. Examples of insulators for use in the compositions and methods described herein include, but are not limited to, the chicken β-globin insulator (see Chung et al., (1993). CELL 74:505; Chung et al., (1997) PROC. NATL. ACAD. SCI., USA 94:575; and Bell et al., 1999. CELL 98:387). Examples of insulator elements include, but are not limited to, an insulator from a β-globin locus, such as chicken HS4.

Non-limiting examples of lentiviral vectors include pLVX-EF1alpha-AcGFP1-C1 (Clontech Catalog #631984), pLVX-EF1alpha-IRES-mCherry (Clontech Catalog #631987), pLVX-Puro (Clontech Catalog #632159), pLVX-IRES-Puro (Clontech Catalog #632186), pLenti6/V5-DEST™ (Thermo Fisher), pLenti6.2/V5-DEST™ (Thermo Fisher), pLKO.1 (Plasmid #10878 at Addgene), pLKO.3G (Plasmid #14748 at Addgene), pSico (Plasmid #11578 at Addgene), pLJM1-EGFP (Plasmid #19319 at Addgene), FUGW (Plasmid #14883 at Addgene), pLVTHM (Plasmid #12247 at Addgene), pLVUT-tTR-KRAB (Plasmid #11651 at Addgene), pLL3.7 (Plasmid #11795 at Addgene), pLB (Plasmid #11619 at Addgene), pWPXL (Plasmid #12257 at Addgene), pWPI (Plasmid #12254 at Addgene), EF.CMV.RFP (Plasmid #17619 at Addgene), pLenti CMV Puro DEST (Plasmid #17452 at Addgene), pLenti-puro (Plasmid #39481 at Addgene), pULTRA (Plasmid #24129 at Addgene), pLX301 (Plasmid #25895 at Addgene), pHIV-EGFP (Plasmid #21373 at Addgene), pLV-mCherry (Plasmid #36084 at Addgene), pLionII (Plasmid #1730 at Addgene), pInducer10-mir-RUP-PheS (Plasmid #44011 at Addgene). These vectors can be modified to be suitable for therapeutic use. For example, a selection marker (e.g., puro, EGFP, or mCherry) can be deleted or replaced with a second exogenous gene of interest. Further examples of lentiviral vectors are disclosed in U.S. Pat. Nos. 7,629,153, 7,198,950, 8,329,462, 6,863,884, 6,682,907, 7,745,179, 7,250,299, 5,994,136, 6,287,814, 6,013,516, 6,797,512, 6,544,771, 5,834,256, 6,958,226, 6,207,455, 6,531,123, and 6,352,694, and PCT Publication No. WO2017/091786.

Adenoviral Vectors

In certain embodiments, the viral vector can be an adenoviral vector. Adenoviruses are medium-sized (90-100 nm), non-enveloped (naked), icosahedral viruses composed of a nucleocapsid and a double-stranded linear DNA genome. The term "adenovirus" refers to any virus in the genus Adenoviridiae including, but not limited to, human, bovine, ovine, equine, canine, porcine, murine, and simian adenovirus subgenera. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

A human adenovirus can be used as the source of the adenoviral genome for the adenoviral vector. For instance, an adenovirus can be of subgroup A (e.g., serotypes 12, 18, and 31), subgroup B (e.g., serotypes 3, 7, 1 1, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serogroup or serotype. Adenoviral serotypes 1 through 51 are available from the American Type Culture Collection (ATCC, Manassas, Virginia). Non-group C adenoviral vectors, methods of producing non-group C adenoviral vectors, and methods of using non-group C adenoviral vectors are disclosed in, for example, U.S. Pat. Nos. 5,801,030, 5,837, 511, and 5,849,561, and PCT Publication Nos. WO1997/012986 and WO1998/053087.

Non-human adenovirus (e.g., ape, simian, avian, canine, ovine, or bovine adenoviruses) can be used to generate the adenoviral vector (i.e., as a source of the adenoviral genome for the adenoviral vector). For example, the adenoviral vector can be based on a simian adenovirus, including both new world and old world monkeys (see, e.g., Virus Taxonomy: VIIIth Report of the International Committee on Taxonomy of Viruses (2005)). A phylogeny analysis of adenoviruses that infect primates is disclosed in, e.g., Roy et al. (2009) PLoS PATHOG. 5 (7): e1000503. A gorilla adenovirus can be used as the source of the adenoviral genome for the adenoviral vector. Gorilla adenoviruses and adenoviral vectors are described in, e.g., PCT Publication Nos. WO2013/052799, WO2013/052811, and WO2013/052832. The adenoviral vector can also comprise a combination of subtypes and thereby be a "chimeric" adenoviral vector.

The adenoviral vector can be replication-competent, conditionally replication-competent, or replication-deficient. A replication-competent adenoviral vector can replicate in typical host cells, i.e., cells typically capable of being infected by an adenovirus. A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., a promoter. Conditionally-replicating adenoviral vectors are further described in U.S. Pat. No. 5,998,205. A replication-deficient adenoviral vector is an adenoviral vector that requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

In some embodiments, the adenoviral vector is replication-deficient, such that the replication-deficient adenoviral vector requires complementation of at least one replication-essential gene function of one or more regions of the adenoviral genome for propagation (e.g., to form adenoviral vector particles). The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See, e.g., Morsy et al. (1998) PROC. NATL. ACAD. SCI. USA 95:965-976, Chen et al. (1997) PROC. NATL. ACAD. SCI. USA 94:1645-1650, and Kochanek et al. (1999) HUM. GENE THER. 10 (15): 2451-9. Examples of replication-deficient adenoviral vectors are disclosed in U.S. Pat. Nos. 5,837,511, 5,851,806, 5,994,106, 6,127,175, 6,482,616, and 7,195,896, and PCT Publication Nos. WO1994/028152, WO1995/002697, WO1995/016772, WO1995/034671, WO1996/022378, WO1997/012986, WO1997/021826, and WO2003/022311.

The replication-deficient adenoviral vector described herein can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al. (1977) J. GEN. VIROL. 36:59-72), PER.C6 cells (described in, e.g., PCT Publication No. WO1997/000326, and U.S. Pat. Nos. 5,994,128 and 6,033,908), and 293-ORF6 cells (described in, e.g., PCT Publication No. WO1995/034671 and Brough et al. (1997) J. VIROL. 71:9206-9213). Other examples of complementing cell lines to produce the replication-deficient adenoviral vector include complementing cells that have been generated to propagate adenoviral vectors encoding transgenes whose expression inhibits viral growth in host cells (see, e.g., U.S. Patent Publication No. 2008/0233650). Additional examples of complementing cells are described in U.S. Pat. Nos. 6,677,156 and 6,682,929, and PCT Publication No. WO2003/020879. Formulations for adenoviral vector-containing compositions are further described in, for example, U.S. Pat. Nos. 6,225,289, and 6,514,943, and PCT Publication No. WO2000/034444.

Additional examples of adenoviral vectors, and/or methods for making or propagating adenoviral vectors are described in U.S. Pat. Nos. 5,559,099, 5,837,511, 5,846,782, 5,851,806, 5,994,106, 5,994,128, 5,965,541, 5,981,225, 6,040,174, 6,020,191, 6,083,716, 6,113,913, 6,303,362, 7,067,310, and 9,073,980.

Commercially available adenoviral vector systems include the ViraPower™ Adenoviral Expression System available from Thermo Fisher Scientific, the AdEasy™ adenoviral vector system available from Agilent Technologies, and the Adeno-X™ Expression System 3 available from Takara Bio USA, Inc.

Other Viral Vectors

In certain embodiments, the viral vector can be a Herpes Simplex Virus plasmid vector. Herpes simplex virus type-1 (HSV-1) has been demonstrated as a potential useful gene delivery vector system for gene therapy. HSV-1 vectors have been used for transfer of genes to muscle, and have been used for murine brain tumor treatment. Helper virus dependent mini-viral vectors have been developed for easier operation and their capacity for larger insertion (up to 140 kb). Replication incompetent HSV amplicons have been constructed in the art. These HSV amplicons contain large deletions of the HSV genome to provide space for insertion of exogenous DNA. Typically they comprise the HSV-1 packaging site, the HSV-1 "ori S" replication site and the IE 4/5 promoter sequence. These virions are dependent on a helper virus for propagation.

Viral Vector Production

Methods for producing viral vectors are known in the art. Typically, a disclosed virus is produced in a suitable host cell line using conventional techniques including culturing a transfected or infected host cell under suitable conditions so as to allow the production of infectious viral particles. Nucleic acids encoding viral genes and/or tRNAs can be incorporated into plasmids and introduced into host cells through conventional transfection or transformation techniques. Examples of host cells for production of disclosed viruses include human cell lines such as HeLa, Hela-S3, HEK293, 911, A549, HER96, or PER-C6 cells. Specific production and purification conditions will vary depending upon the virus and the production system employed.

In certain embodiments, producer cells may be directly administered to a subject, however, in other embodiments, following production, infectious viral particles are recovered from the culture and optionally purified. Typical purification steps may include plaque purification, centrifugation, e.g., cesium chloride gradient centrifugation, clarification, enzymatic treatment, e.g., benzonase or protease treatment, chromatographic steps, e.g., ion exchange chromatography or filtration steps.

IV. Pharmaceutical Compositions

For therapeutic use, a tRNA and/or expression vector can be combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (See *Remington's Pharmaceutical Sciences*, 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1:10-29). In certain embodiments, the composition does not comprise a nanoparticle or an aminolipid delivery compound, e.g., as described in U.S. Patent Publication No. 2017/0354672. In certain embodiments, the tRNA or expression vector introduced into the cell or administered to the subject is not conjugated to or associated with another moiety, e.g., a carrier particle, e.g., an aminolipid particle. As used herein, the term "conjugated," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (-)-3-hydroxybutyric acid. Sustained release compositions may also include liposomes that can be prepared by any of several methods known in the art.

Pharmaceutical compositions containing a tRNA and/or expression vector disclosed herein can be presented in a dosage unit form and can be prepared by any suitable method. A pharmaceutical composition can be formulated to be compatible with its intended route of administration. Examples of routes of administration are intravenous (IV), intradermal, inhalation, transdermal, topical, transmucosal, intrathecal and rectal administration. In certain embodiments, a tRNA and/or expression vector is administered intrathecally. In certain embodiments, a tRNA and/or expression vector is administered by injection. Formulations can be prepared by methods known in the pharmaceutical art. For example, see *Remington's Pharmaceutical Sciences*, 18th ed. (Mack Publishing Company, 1990). Formulation components for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, carriers include physiological saline, bacteriostatic water, Cremophor EL™ (BASF, Parsippany, NJ) or phosphate buffered saline (PBS). The carrier can be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

In general, any method of delivering a nucleic acid molecule can be adapted for use with a tRNA (see e.g., Akhtar et al. (1992) TRENDS CELL. BIOL. 2 (5): 139-144 and PCT Publication No. WO94/02595). The tRNA can be modified or alternatively delivered using a drug delivery system to prevent the rapid degradation of the tRNA by endo- and exo-nucleases in vivo. tRNA molecules can be modified by chemical conjugation to lipophilic groups such as cholesterol to enhance cellular uptake and prevent degradation. tRNA molecules can also be conjugated to or otherwise associated with an aptamer. A tRNA can also be delivered using drug delivery systems such as a nanoparticle, a dendrimer, a polymer, liposomes, or a cationic delivery system. Positively charged cationic delivery systems facilitate binding of a tRNA molecule (negatively charged) and also enhance interactions at the negatively charged cell membrane to permit efficient uptake of a tRNA by the cell. Cationic lipids, dendrimers, or polymers can either be bound to the RNA, e.g., tRNA, or induced to form a vesicle or micelle (see e.g., Kim et al. (2008) JOURNAL OF CONTROLLED RELEASE 129 (2): 107-116) that encases the RNA. Methods for making and administering cationic-RNA complexes are well within the abilities of one skilled in the art (see, e.g., Sorensen et al. (2003) J. MOL. BIOL 327:761-766; Verma et al. (2003) CLIN. CANCER RES. 9:1291-1300; Arnold et al. (2007) J. HYPERTENS. 25:197-205). Some non-limiting examples of drug delivery systems useful for systemic delivery of RNAs, e.g., tRNAs include DOTAP (Sorensen et al. (2003) supra; Verma et al. (2003), supra), Oligofectamine, solid nucleic acid lipid particles (Zimmermann et al. (2006) NATURE 441:111-114), cardiolipin (Chien et al. (2005) CANCER GENE THER. 12:321-328; Pal et al. (2005) INT J. ONCOL. 26:1087-1091), polyethyleneimine (Bonnet et al. (2008) PHARM. RES. 25 (12): 2972-82; Aigner (2006) J. BIOMED. BIOTECHNOL. 71659), Arg-Gly-Asp (RGD) peptides (Liu (2006) MOL. PHARM. 3:472-487), and polyamidoamines (Tomalia et al. (2007) BIOCHEM. SOC. TRANS. 35:61-67; Yoo et al. (1999) PHARM. RES. 16:1799-1804). In certain embodiments, a tRNA forms a complex with cyclodextrin for systemic administration. Methods for administration and pharmaceutical compositions of RNAs and cyclodextrins can be found in U.S. Pat. No. 7,427,605.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In some embodiments, the pharmaceutical composition is administered subcutaneously and in an even more preferred embodiment intravenously. Preparations for parenteral administration include sterile aqueous or non-aqueous solutions, suspensions, and emulsions.

Generally, a therapeutically effective amount of active component, for example, a tRNA and/or expression vector, is in the range of 0.1 mg/kg to 100 mg/kg, e.g., 1 mg/kg to 100 mg/kg, 1 mg/kg to 10 mg/kg. In certain embodiments, a therapeutically effective amount of a viral expression vector is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life, and the disease being treated. Examples of dosing frequencies are once per day, once per week and once every two weeks. One example of a route of administration is parenteral, e.g., intravenous infusion.

V. Therapeutic Uses

The compositions and methods disclosed herein can be used to treat a haploinsufficiency disorder in a subject. As used herein, the term haploinsufficiency disorder refers to a disorder that is mediated, enhanced or otherwise facilitated by or associated with a haploinsufficiency, i.e., a condition where a diploid subject has only a single functional copy of a gene and the single functional copy of the gene does not produce enough of a gene product (e.g., a protein) for proper gene function. As used herein, a haploinsufficient gene refers to a gene that requires both alleles for proper gene function. Examples of haploinsufficiency disorders include 5q-syndrome, Adams-Oliver syndrome 1, Adams-Oliver syndrome 3, Adams-Oliver syndrome 5, Adams-Oliver syndrome 6, Alagille syndrome 1, Autoimmune lymphoproliferative syndrome type IA, Autoimmune lymphoproliferative syndrome type V, Autosomal dominant deafness-2A, Brain malformations with or without urinary tract defects (BRMUTD), Carney complex type 1, CHARGE syndrome, Cleidocranial dysplasia, Currarino syndrome, Denys-Drash syndrome/Frasier syndrome, Developmental delay, intellectual disability, obesity, and dysmorphic features (DIDOD), DiGeorge syndrome (TBX1-associated), Dravet syndrome, Duane-radial ray syndrome, Ehlers-Danlos syndrome (classic-like), Ehlers-Danlos syndrome (vascular type), Feingold syndrome 1, Frontotemporal lobar degeneration with TDP43 inclusions (FTLD-TDP), GRN-related, GLUT1 deficiency syndrome, Greig cephalopolysyndactyly syndrome, Hereditary hemorrhagic telangiectasia type 1, Holoprosencephaly 3, Holoprosencephaly 4, Holoprosencephaly 5, Holt-Oram syndrome, Hypoparathyroidism, sensorineural deafness, and renal disease (HDR), Kleefstra syndrome 1, Klippel-Trenaunay syndrome (AAGF-related), Leri-Weill dyschondrosteosis, Marfan syndrome, Mental retardation and distinctive facial features with or without cardiac defects (MRFACD), Mental retardation, autosomal dominant 1, Mental retardation, autosomal dominant 19, Mental retardation, autosomal dominant 29, Nail-patella syndrome (NPS), Phelan-McDermid syndrome, Pitt-Hopkins syndrome, Primary pulmonary hypertension 1, Rett syndrome (congenital variant), Smith-Magenis syndrome (RAI1-associated), Sotos syndrome 1, Sotos syndrome 2, Stickler syndrome type I, Supravalvular aortic stenosis, SYNGAP1-related intellectual disability, Treacher Collins syndrome, Trichorhinophalangeal syndrome type I, Ulnar-mammary syndrome, van der Woude syndrome 1, Waardenburg syndrome type 1, Waardenburg syndrome type 2A, and Waardenburg syndrome type 4C. Examples of haploinsufficiency disorders, including the associated haploinsufficient genes, are depicted in TABLE 1 and TABLE 2.

This disclosure provides a method of treating a haploinsufficiency disorder in a subject in need thereof. The method comprises administering to the subject an effective amount of a tRNA and/or expression vector, e.g., a tRNA and/or expression vector disclosed herein, either alone or in a combination with another therapeutic agent to treat the haploinsufficiency disorder in the subject.

In certain embodiments, wherein the haploinsufficiency disorder is Dravet syndrome, the method reduces seizure frequency, seizure severity, and/or cognitive impairment in the subject. For example, in certain embodiments, the method reduces seizure frequency in the subject by at least 10%, 20%, 30%, 40%, 50%, 60%, 70%, 80%, 90% or 100% over the period of, e.g., a day, a week, or a month. In certain embodiments, the method reduces seizure frequency by 50% over the period of, e.g., a day, a week, or a month.

The term "effective amount" as used herein refers to the amount of an active agent (e.g., recombinant polypeptide and/or multimeric protein) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a method or composition described herein is administered in combination with one or more additional therapies, e.g., DIACOMIT® (stiripentol), EPIODOLEX® (cannabidiol), a ketogenic diet, ONFI® (clobazam), TOPAMAX® (topiramate), or valproic acid. For example, during the treatment of Dravet Syndrome, a method or composition described herein is administered in combination with one or more additional therapies, e.g., DIACOMIT® (stiripentol), EPIODOLEX® (cannabidiol), a ketogenic diet, ONFI® (clobazam), TOPAMAX® (topiramate), or valproic acid.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1—tRNA Expression to Enhance Expression of Wildtype SCN1A Transcript

In this Example, the least optimal and most overrepresented codons in SCN1A were determined. Expression of the cognate tRNAs for these codons may enhance SCN1A expression and treat Dravet syndrome.

First, percentage codon usage for each codon in the SCN1A gene was determined. Next the optimality for each codon in the SCN1A gene was determined using the tRNA adaptive index (tAI). tAI is an estimate of translation efficiency for each codon that takes into account estimates of cellular concentration of tRNA (based on tRNA gene copy numbers) and efficiencies of decoding, with a higher tAI value indicating a more optimal codon. tAI is described, for example, in dos Reis et al. (2004) NUCLEIC ACIDS RES. 32 (17): 5036-5044, and Mahlab et al. (2014) PLoS COMPUT. BIOL. 10 (1): e1003294. For the calculations in this example, a modified tAI value was used that is based on a direct quantification of tRNA levels in HEK293 cells (as given in Zheng et al. (2015) NAT. METHODS 12 (9): 835-837) in place of estimates based on tRNA gene copy number.

The percentage codon usage value was multiplied by the inverse of the tAI value to give a score for each codon in the SCN1A gene. A summary of the results is shown in TABLE 3. Generally, codons with the highest scores are the least optimal and most enriched in SCN1A relative to the transcriptome, and cognate tRNAs for these codons are the best candidates to enhance SCN1A expression.

TABLE 3

| Codon | % Codon Usage | tAI | 1/tAI | (% Codon Usage) × (1/tAI) |
|---|---|---|---|---|
| ATA (Ile) | 1.642 | 0.035 | 28.663 | 47.059 |
| AGA (Arg) | 1.393 | 0.03 | 33.342 | 46.447 |
| CTT (Leu) | 2.04 | 0.045 | 22.345 | 45.58 |
| CTC (Leu) | 1.244 | 0.032 | 31.035 | 38.601 |
| TAT (Tyr) | 1.841 | 0.053 | 18.935 | 34.856 |
| GAA (Glu) | 4.577 | 0.142 | 7.047 | 32.256 |
| CTA (Leu) | 1.343 | 0.043 | 23.305 | 31.306 |
| TTT (Phe) | 3.632 | 0.13 | 7.691 | 27.931 |
| AAT (Asn) | 3.234 | 0.132 | 7.575 | 24.496 |
| CCT (Pro) | 1.244 | 0.055 | 18.139 | 22.561 |
| GCA (Ala) | 1.841 | 0.083 | 11.991 | 22.072 |
| TGT (Cys) | 1.443 | 0.069 | 14.399 | 20.775 |
| CCC (Pro) | 0.746 | 0.04 | 25.193 | 18.801 |
| TCC (Ser) | 1.642 | 0.088 | 11.402 | 18.72 |
| GGA (Gly) | 1.99 | 0.109 | 9.16 | 18.228 |
| ATC (Ile) | 2.388 | 0.149 | 6.715 | 16.035 |
| ATT (Ile) | 3.284 | 0.207 | 4.84 | 15.893 |
| TTC (Phe) | 3.433 | 0.22 | 4.537 | 15.576 |
| CCA (Pro) | 1.642 | 0.117 | 8.566 | 14.064 |
| TTG (Leu) | 1.741 | 0.126 | 7.945 | 13.835 |
| TAC (Tyr) | 1.194 | 0.089 | 11.175 | 13.343 |
| AGT (Ser) | 1.692 | 0.128 | 7.793 | 13.183 |
| GAG (Glu) | 2.189 | 0.166 | 6.008 | 13.151 |
| ACA (Thr) | 1.642 | 0.133 | 7.522 | 12.349 |
| GAT (Asp) | 2.786 | 0.233 | 4.299 | 11.978 |
| AAA (Lys) | 3.532 | 0.3 | 3.338 | 11.791 |
| TCT (Ser) | 1.244 | 0.122 | 8.209 | 10.211 |
| AGG (Arg) | 1.045 | 0.107 | 9.344 | 9.763 |
| AAC (Asn) | 2.04 | 0.224 | 4.469 | 9.116 |
| ACT (Thr) | 1.99 | 0.218 | 4.579 | 9.113 |
| CAA (Gln) | 1.443 | 0.163 | 6.145 | 8.866 |
| TGG (Trp) | 1.343 | 0.155 | 6.469 | 8.69 |
| CTG (Leu) | 2.438 | 0.299 | 3.34 | 8.143 |
| AAG (Lys) | 2.338 | 0.287 | 3.482 | 8.142 |
| ACC (Thr) | 1.194 | 0.157 | 6.36 | 7.594 |
| GCC (Ala) | 1.592 | 0.221 | 4.518 | 7.192 |
| GTA (Val) | 1.244 | 0.179 | 5.572 | 6.93 |
| AGC (Ser) | 1.393 | 0.217 | 4.598 | 6.406 |
| GCT (Ala) | 1.841 | 0.307 | 3.253 | 5.987 |
| GAC (Asp) | 2.338 | 0.394 | 2.537 | 5.931 |
| TTA (Leu) | 1.095 | 0.187 | 5.351 | 5.857 |
| CGC (Arg) | 0.448 | 0.078 | 12.852 | 5.755 |
| ATG (Met) | 3.483 | 0.674 | 1.484 | 5.167 |
| CGA (Arg) | 1.045 | 0.205 | 4.867 | 5.085 |
| GGG (Gly) | 0.995 | 0.201 | 4.978 | 4.953 |
| ACG (Thr) | 0.597 | 0.13 | 7.681 | 4.586 |
| TCA (Ser) | 1.194 | 0.268 | 3.731 | 4.455 |
| GGT (Gly) | 0.995 | 0.25 | 3.995 | 3.975 |
| CAG (Gln) | 1.642 | 0.495 | 2.02 | 3.316 |
| CAT (His) | 0.547 | 0.169 | 5.902 | 3.23 |
| CGT (Arg) | 0.348 | 0.108 | 9.254 | 3.223 |
| GTT (Val) | 1.741 | 0.54 | 1.851 | 3.223 |
| GTC (Val) | 1.244 | 0.389 | 2.57 | 3.197 |
| TGC (Cys) | 0.348 | 0.118 | 8.496 | 2.959 |
| GCG (Ala) | 0.299 | 0.104 | 9.597 | 2.865 |
| GGC (Gly) | 1.194 | 0.424 | 2.357 | 2.815 |
| GTG (Val) | 2.637 | 1 | 1 | 2.637 |
| CAC (His) | 0.597 | 0.287 | 3.482 | 2.079 |
| CGG (Arg) | 0.348 | 0.198 | 5.05 | 1.759 |
| TCG (Ser) | 0.199 | 0.125 | 7.974 | 1.587 |
| CCG (Pro) | 0.1 | 0.109 | 9.204 | 0.916 |

Example 2—tRNA Expression to Enhance Expression of Wildtype SCN1A Transcript

In this Example, the ability of ectopic delivery of select transfer RNAs (tRNAs) to enhance expression of wildtype SCN1A in cultured cells was evaluated.

ATA (Ile), GTA (Val), and AGA (Arg) were selected as exemplary non-optimal codons in the SCN1A gene. A nucleotide sequence encoding an ATA tRNA (tRNA$^{ATA}$) is depicted in SEQ ID NO: 1, a nucleotide sequence encoding an GTA tRNA (tRNA$^{GTA}$) is depicted in SEQ ID NO: 2, and a nucleotide sequence encoding an AGA tRNA (tRNA$^{AGA}$) is depicted in SEQ ID NO: 3, The SCN1A open reading frame was amplified by RT-PCR from human brain RNA (Clontech) using primers that contain a KpnI site in the forward primer and a NotI site in the reverse primer. SCN1A ORF was then cloned between the promoter and SV40 poly (A) site of pTRE-Tight (Clontech) using KpnI and NotI sites.

tRNA$^{ATA}$, tRNA$^{GTA}$, and tRNA$^{AGA}$ gene sequences (including the tRNA coding sequence along with 200 base pairs (bp) of flanking genomic DNA sequence) were ordered as gBlocks (IDT) with an XhoI site in the 5' end and a PciI site in the 3' end. The tRNA$^{ATA}$ gene sequence (including the tRNA coding sequence along with 200 bp of flanking genomic DNA sequence) is depicted in SEQ ID NO: 4, the tRNA$^{GTA}$ gene sequence (including the tRNA coding sequence along with 200 bp of flanking genomic DNA sequence) is depicted in SEQ ID NO: 5, and the tRNA$^{AGA}$ gene sequence (including the tRNA coding sequence along with 200 base pairs (bp) of flanking genomic DNA sequence) is depicted in SEQ ID NO: 6.

All tRNA gene sequences were individually cloned into pTRE-Tight (Clontech) using XhoI and PciI sites such that only the ampicillin resistance gene and Col E1 origin were left from pTRE-Tight. Entire tRNA gene sequences were confirmed by sequencing.

HEK293 cells were plated in DMEM with 10% FBS at 300,000 cells per well of a 6-well plate. 24 hours later, each well was either mock transfected (no DNA), or transfected with 100 ng of SCN1A plasmid and either 0, 100, 200, or 300 ng of each tRNA using 1, 4, 7, or 10 µL of Enhancer and 10 µL of Effectene (Qiagen). Transfected cells were incubated for 24 hours, then harvested directly into Trizol (ThermoFisher) for total RNA preparation according to the manufacturer's protocol. 2 µg of total RNA from each condition was then treated with 4 U of Turbo DNase (ThermoFisher) and cleaned up by precipitation with 2.5 M lithium chloride. cDNA was prepared from 300 ng of DNase-treated RNA in a 10 µL total reaction volume using SuperScript III First Strand Synthesis Supermix and random primers (ThermoFisher) according to the manufacturer's instructions. qPCR was performed in a 10 µL total reaction volume using SYBR Advantage qPCR Premix (Takara), primers for SCN1A and GAPDH, and one-twentieth of cDNA per reaction in a Step One Real Time PCR System (Applied Biosystems).

Figure 3:
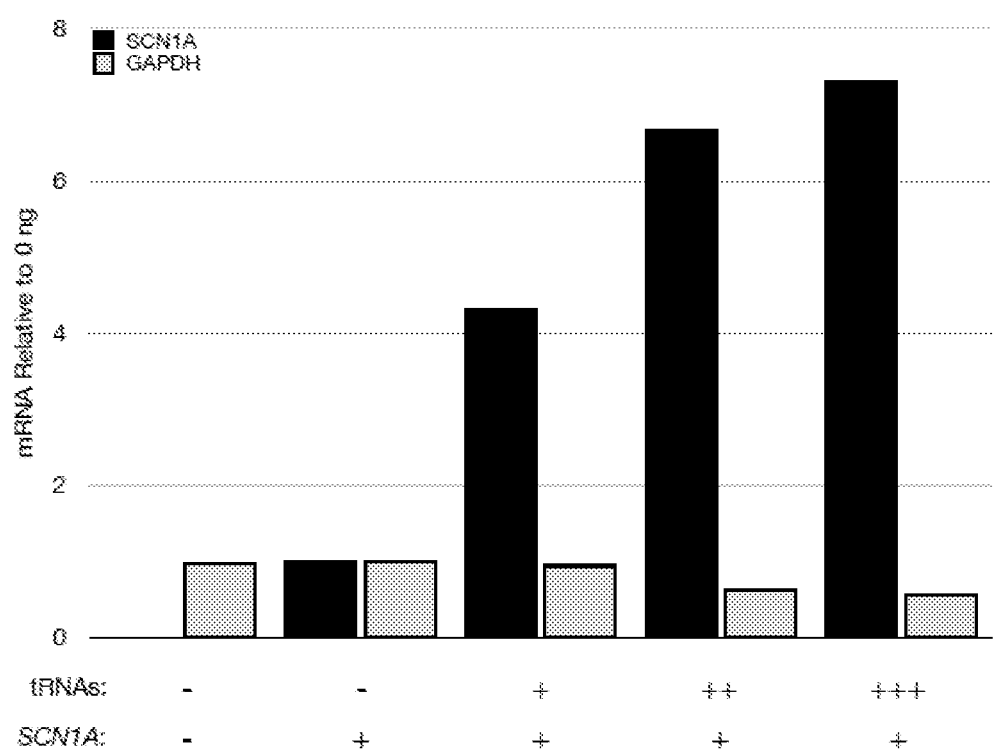
FIG. 3 is a graph showing quantification of SCN1A and GAPDH mRNA levels in HEK293 cells after expression of tRNA$^{ATA}$, tRNA$^{GTA}$, and tRNA$^{AGA}$. Indicated values were calculated relative to cells expressing SCN1A but no tRNA by the $^{\Delta\Delta}$Ct method. + indicates 100 ng DNA for each tRNA; ++ indicates 200 ng DNA for each tRNA; and +++ indicates 300 ng DNA each tRNA.

As shown in FIG. 3, across a range of doses, ectopic tRNA expression had minimal effect on an endogenous transcript, GAPDH. However, ectopic tRNA expression resulted in a roughly linear increase in SCN1A expression, up to 7-fold at the highest dose of tRNAs tested (FIG. 3). No overt toxicity to cells was observed except at the highest concentration of tRNAs.

Together, these results indicate that expression of an mRNA transcript, e.g., an SCN1A transcript, can be increased by ectopic expression of tRNAs cognate to non-optimal codons within that transcript.

Example 3—tRNA Expression to Enhance Expression of Haploinsufficient Genes

In this Example, the least optimal and most overrepresented codons in a range of genes associated with haploinsufficieny disorders were determined. Expression of the cognate tRNAs for these codons may enhance gene expression and treat the haploinsufficieny disorder.

As described in Example 1, percentage codon usage for each codon in the gene was determined. Next the optimality for each codon in the gene was determined using the tRNA adaptive index (tAI). tAI is an estimate of translation efficiency for each codon that takes into account estimates of cellular concentration of tRNA (based on tRNA gene copy numbers) and efficiencies of decoding, with a higher tAI value indicating a more optimal codon. tAI is described, for example, in dos Reis et al. (2004) NUCLEIC ACIDS RES. 32 (17): 5036-5044, and Mahlab et al. (2014) PLoS COMPUT. BIOL. 10 (1): e1003294. The percentage codon usage value was multiplied by the inverse of the tAI value to give a score for each codon in the gene. Generally, codons with the highest scores are the least optimal and most enriched in the gene relative to the transcriptome, and cognate tRNAs for these codons are the best candidates to enhance gene expression.

The three least optimal and most overrepresented codons in the indicated genes are shown in TABLE 4, and the ten least optimal and most overrepresented codons in the indicated genes are shown in TABLE 5.

TABLE 4

| Disorder | Gene | Codons |
|---|---|---|
| 5q-syndrome | RPS14 | GGT (Gly), CGC (Arg), ACC (Thr) |
| Adams-Oliver syndrome 1 | ARHGAP31 | TCA (Ser), GAG (Glu), AGC (Ser) |
| Adams-Oliver syndrome 3 | RBPJ | ACA (Thr), TCA (Ser), TTT (Phe) |
| Adams-Oliver syndrome 5 | NOTCH1 | CCC (Pro), CTG (Leu), GGC (Gly) |
| Adams-Oliver syndrome 6 | DLL4 | CGC (Arg), CTG (Leu), ACC (Thr) |
| Alagille syndrome 1 | JAG1 | TGT (Cys), GAT (Asp), CCC (Pro) |
| Autoimmune lymphoproliferative syndrome type IA | FAS | CAT (His), AGA (Arg), GAA (Glu) |
| Autoimmune lymphoproliferative syndrome type V | CTLA4 | TTT (Phe), CTC (Leu), CCA (Pro) |
| Autosomal dominant deafness-2A | KCNQ4 | CGC (Arg), CTG (Leu), TCC (Ser) |
| Brain malformations with or without urinary tract defects (BRMUTD) | NFIA | AGT (Ser), CCA (Pro), ACA (Thr) |
| Carney complex type 1 | PRKARIA | GAT (Asp), TTT (Phe), GAG (Glu) |
| CHARGE syndrome | CHD7 | GAT (Asp), TCA (Ser), GAA (Glu) |
| Cleidocranial dysplasia | RUNX2 | CCC (Pro), CCG (Pro), TCC (Ser) |
| Currarino syndrome | MNX1 | GCG (Ala), GGC (Gly), CCG (Pro) |
| Denys-Drash syndrome / Frasier syndrome | WT1 | CCC (Pro), CCG (Pro), AGC (Ser) |
| Developmental delay, intellectual disability, obesity, and dysmorphic features (DIDOD) | PHIP | GAT (Asp), TCA (Ser), AGT (Ser) |
| DiGeorge syndrome (TBX1-associated) | TBX1 | CCG (Pro), CCC (Pro), GCG (Ala) |
| Dravet syndrome | SCN1A | TTT (Phe), CTA (Leu), GAT (Asp) |
| Duane-radial ray syndrome | SALL4 | ACC (Thr), AGC (Ser), TCC (Ser) |
| Ehlers-Danlos syndrome (classic-like) | TNXB | CCC (Pro), CGC (Arg), GAG (Glu) |
| Ehlers-Danlos syndrome (vascular type) | COL3A1 | GGT (Gly), GGA (Gly), CCT (Pro) |
| Feingold syndrome 1 | MYCN | CCC (Pro), CCG (Pro), GAG (Glu) |
| Frontotemporal lobar degeneration with TDP43 inclusions (FTLD-TDP), GRN-related | GRN | CCC (Pro), ACC (Thr), CAC (His) |
| GLUT1 deficiency syndrome | SLC2A1 | CTG (Leu), TTC (Phe), CCC (Pro) |

TABLE 4-continued

| Disorder | Gene | Codons |
|---|---|---|
| Greig cephalopolysyndactyly syndrome | GLI3 | AGC (Ser), TCC (Ser), CAT (His) |
| Hereditary hemorrhagic telangiectasia type 1 | ENG | AGC (Ser), CTG (Leu), CTC (Leu) |
| Holoprosencephaly 3 | SHH | CTG (Leu), CGC (Arg), GCG (Ala) |
| Holoprosencephaly 4 | TGIF1 | TCC (Ser), CCA (Pro), CTA (Leu) |
| Holoprosencephaly 5 | ZIC2 | GCG (Ala), CAC (His), GGC (Gly) |
| Holt-Oram syndrome | TBX5 | TCC (Ser), CCC (Pro), CAT (His) |
| Hypoparathyroidism, sensorineural deafness, and renal disease (HDR) | GATA3 | TCC (Ser), CCC (Pro), CAC (His) |
| Kleefstra syndrome 1 | EHMT1 | GAG (Glu), CTG (Leu), AGC (Ser) |
| Klippel-Trenaunay syndrome (AAGF-related) | AGGF1 | GAT (Asp), AGT (Ser), GAA (Glu) |
| Leri-Weill dyschondrosteosis | SHOX | CTG (Leu), CGC (Arg), GAG (Glu) |
| Marfan syndrome | FBN1 | GAT (Asp), TGT (Cys), GGA (Gly) |
| Mental retardation and distinctive facial features with or without cardiac defects (MRFACD) | MED13L | GAT (Asp), AGT (Ser), TCA (Ser) |
| Mental retardation, autosomal dominant 1 | MBD5 | AGT (Ser), TCA (Ser), CCA (Pro) |
| Mental retardation, autosomal dominant 19 | CTNNB1 | GAT (Asp), GGT (Gly), CAT (His) |
| Mental retardation, autosomal dominant 29 | SETBP1 | AGT (Ser), CCA (Pro), CCC (Pro) |
| Nail-patella syndrome (NPS) | LMX1B | TCC (Ser), CTG (Leu), GAG (Glu) |
| Phelan-McDermid syndrome | SHANK3 | CGC (Arg), CCC (Pro), CTG (Leu) |
| Pitt-Hopkins syndrome | TCF4 | TCA (Ser), CAT (His), AGT (Ser) |
| Primary pulmonary hypertension 1 | BMPR2 | ACA (Thr), TCA (Ser), GAT (Asp) |
| Rett syndrome (congenital variant) | FOXG1 | CCG (Pro), CCC (Pro), CAC (His) |
| Smith-Magenis syndrome (RAI1-associated) | RAI1 | CCC (Pro), TCC (Ser), AGC (Ser) |
| Sotos syndrome 1 | NSD1 | TCA (Ser), GAT (Asp), AGT (Ser) |
| Sotos syndrome 2 | NFIX | TCC (Ser), CTG (Leu), TCA (Ser) |
| Stickler syndrome type I | COL2A1 | GGT (Gly), CCT (Pro), GGA (Gly) |
| Supravalvular aortic stenosis | ELN | GGA (Gly), GGT (Gly), GCA (Ala) |
| SYNGAP1-related intellectual disability | SYNGAP1 | CTG (Leu), GAG (Glu), CGG (Arg) |
| Treacher Collins syndrome | TCOF1 | TCA (Ser), GAG (Glu), AGT (Ser) |
| Trichorhinophalangeal syndrome type I | TRPS1 | AGT (Ser), TCA (Ser), CAT (His) |
| Ulnar-mammary syndrome | TBX3 | TCC (Ser), GCG (Ala), CCG (Pro) |
| van der Woude syndrome 1 | IRF6 | CCC (Pro), CTG (Leu), GAT (Asp) |
| Waardenburg syndrome type 1 | PAX3 | AGC (Ser), ACC (Thr), CCC (Pro) |
| Waardenburg syndrome type 2A | MITF | TCC (Ser), CAT (His), CAA (Gln) |
| Waardenburg syndrome type 4C | SOX10 | CCC (Pro), GAG (Glu), TCA (Ser) |

TABLE 5

| Disorder | Gene | Codons |
|---|---|---|
| 5q-syndrome | RPS14 | GGT (Gly), CGC (Arg), ACC (Thr), GTC (Val), GAT (Asp), GGA (Gly), TTT (Phe), GAA (Glu), CAT (His), AGG (Arg) |
| Adams-Oliver syndrome 1 | ARHGAP31 | TCA (Ser), GAG (Glu), AGC (Ser), CCA (Pro), CTG (Leu), CCC (Pro), CCT (Pro), ACC (Thr), TCC (Ser), AGG (Arg) |
| Adams-Oliver syndrome 3 | RBPJ | ACA (Thr), TCA (Ser), TTT (Phe), GAT (Asp), AGT (Ser), CCA (Pro), CGA (Arg), CAT (His), GTA (Val), GGA (Gly) |
| Adams-Oliver syndrome 5 | NOTCH1 | CCC (Pro), CTG (Leu), GGC (Gly), ACC (Thr), CGC (Arg), GAG (Glu), AGC (Ser), GAC (Asp), TCC (Ser), CCG (Pro) |
| Adams-Oliver syndrome 6 | DLL4 | CGC (Arg), CTG (Leu), ACC (Thr), GGC (Gly), CCC (Pro), TCC (Ser), AGC (Ser), CGG (Arg), TGT (Cys), CCA (Pro) |
| Alagille syndrome 1 | JAG1 | TGT (Cys), GAT (Asp), CCC (Pro), AGT (Ser), ACC (Thr), TCC (Ser), GGC (Gly), GAC (Asp), GAG (Glu), TCA (Ser) |
| Autoimmune lymphoproliferative syndrome type IA | FAS | CAT (His), AGA (Arg), GAA (Glu), ACA (Thr), CAA (Gln), ACC (Thr), TTG (Leu), ACT (Thr), CTA (Leu), GTT (Val) |
| Autoimmune lymphoproliferative syndrome type V | CTLA4 | TTT (Phe), CTC (Leu), CCA (Pro), ACC (Thr), ACA (Thr), AGC (Ser), TAT (Tyr), CTA (Leu), CTG (Leu), GAT (Asp) |
| Autosomal dominant deafness-2A | KCNQ4 | CGC (Arg), CTG (Leu), TCC (Ser), CGG (Arg), AGC (Ser), CCC (Pro), GGC (Gly), ACC (Thr), GTC (Val), GAG (Glu) |
| Brain malformations with or without urinary tract defects (BRMUTD) | NFIA | AGT (Ser), CCA (Pro), ACA (Thr), TCA (Ser), CAT (His), CCC (Pro), TTT (Phe), TCC (Ser), CGC (Arg), GAT (Asp) |
| Carney complex type 1 | PRKARIA | GAT (Asp), TTT (Phe), GAG (Glu), AGA (Arg), TCA (Ser), GAA (Glu), AGT (Ser), CGA (Arg), GCA (Ala), CGT (Arg) |
| CHARGE syndrome | CHD7 | GAT (Asp), TCA (Ser), GAA (Glu), TTT (Phe), CCA (Pro), AGT (Ser), GAG (Glu), CTA (Leu), CAT (His), CAA (Gln) |
| Cleidocranial dysplasia | RUNX2 | CCC (Pro), CCG (Pro), TCC (Ser), ACC (Thr), GCG (Ala), CGC (Arg), CTG (Leu), CGG (Arg), AGC (Ser), AGT (Ser) |
| Currarino syndrome | MNX1 | GCG (Ala), GGC (Gly), CCG (Pro), CTG (Leu), CGC (Arg), CCC (Pro), TCG (Ser), GCC (Ala), AGC (Ser), GAG (Glu) |
| Denys-Drash syndrome/ Frasier syndrome | WT1 | CCC (Pro), CCG (Pro), AGC (Ser), CAC (His), GCG (Ala), CTG (Leu), ACC (Thr), TCC (Ser), CAT (His), GGT (Gly) |
| Developmental delay, intellectual disability, obesity, and dysmorphic features (DIDOD) | PHIP | GAT (Asp), TCA (Ser), AGT (Ser), AGA (Arg), CAT (His), ATA (Ile), TTT (Phe), CTA (Leu), GAA (Glu), CAA (Gln) |
| DiGeorge syndrome (TBX1-associated) | TBX1 | CCG (Pro), CCC (Pro), GCG (Ala), GCC (Ala), CAC (His), CTG (Leu), GGC (Gly), CGC (Arg), AGC (Ser), CGG (Arg) |
| Dravet syndrome | SCN1A | TTT (Phe), CTA (Leu), GAT (Asp), AGT (Ser), GAA (Glu), ATA (Ile), TCA (Ser), ACA (Thr), TTC (Phe), TAT (Tyr) |

TABLE 5-continued

| Disorder | Gene | Codons |
|---|---|---|
| Duane-radial ray syndrome | SALL4 | ACC (Thr), AGC (Ser), TCC (Ser), CCC (Pro), GAG (Glu), GGT (Gly), GAT (Asp), CTC (Leu), CAC (His), CAG (Gln) |
| Ehlers-Danlos syndrome (classic-like) | TNXB | CCC (Pro), CGC (Arg), GAG (Glu), ACC (Thr), CTG (Leu), ACA (Thr), GGG (Gly), TCC (Ser), GGC (Gly), GTG (Val) |
| Ehlers-Danlos syndrome (vascular type) | COL3A1 | GGT (Gly), GGA (Gly), CCT (Pro), CCA (Pro), GAT (Asp), AGT (Ser), GAA (Glu), CCC (Pro), GGC (Gly), AGA (Arg) |
| Feingold syndrome 1 | MYCN | CCC (Pro), CCG (Pro), GAG (Glu), CGC (Arg), TCC (Ser), AGC (Ser), GCC (Ala), ACC (Thr), CTG (Leu), GAT (Asp) |
| Frontotemporal lobar degeneration with TDP43 inclusions (FTLD-TDP), GRN-related | GRN | CCC (Pro), ACC (Thr), CAC (His), TCC (Ser), GAT (Asp), TGC (Cys), CTG (Leu), TGT (Cys), AGC (Ser), CGC (Arg) |
| GLUT1 deficiency syndrome | SLC2A1 | CTG (Leu), TTC (Phe), CCC (Pro), TCC (Ser), GGC (Gly), CGC (Arg), ACC (Thr), ATC (Ile), CTC (Leu), GTG (Val) |
| Greig cephalopolysyndactyly syndrome | GLI3 | AGC (Ser), TCC (Ser), CAT (His), CCC (Pro), TCA (Ser), CCG (Pro), ACC (Thr), CCA (Pro), CTC (Leu), CTG (Leu) |
| Hereditary hemorrhagic telangiectasia type 1 | ENG | AGC (Ser), CTG (Leu), CTC (Leu), ACC (Thr), CCC (Pro), TCC (Ser), GTC (Val), GAG (Glu), TCA (Ser), GGC (Gly) |
| Holoprosencephaly 3 | SHH | CTG (Leu), CGC (Arg), GCG (Ala), TCG (Ser), ACC (Thr), GGC (Gly), GAG (Glu), CTC (Leu), GAC (Asp), CAC (His) |
| Holoprosencephaly 4 | TGIF1 | TCC (Ser), CCA (Pro), CTA (Leu), CCG (Pro), TCA (Ser), CGC (Arg), CCC (Pro), ACA (Thr), TCT (Ser), CTC (Leu) |
| Holoprosencephaly 5 | ZIC2 | GCG (Ala), CAC (His), GGC (Gly), TCC (Ser), CCG (Pro), CCC (Pro), AGC (Ser), CGC (Arg), TCG (Ser), TTC (Phe) |
| Holt-Oram syndrome | TBX5 | TCC (Ser), CCC (Pro), CAT (His), ACC (Thr), AGC (Ser), CAC (His), CTA (Leu), TTT (Phe), CCT (Pro), GAG (Glu) |
| Hypoparathyroidism, sensorineural deafness, and renal disease (HDR) | GATA3 | TCC (Ser), CCC (Pro), CAC (His), CCG (Pro), ACC (Thr), TCG (Ser), AGC (Ser), CTG (Leu), CTC (Leu), AGG (Arg) |
| Kleefstra syndrome 1 | EHMT1 | GAG (Glu), CTG (Leu), AGC (Ser), CCC (Pro), GAC (Asp), CTC (Leu), ACC (Thr), TCC (Ser), AGG (Arg), TCA (Ser) |
| Klippel-Trenaunay syndrome (AAGF-related) | AGGF1 | GAT (Asp), AGT (Ser), GAA (Glu), TCA (Ser), CAT (His), ACA (Thr), TAT (Tyr), CAA (Gln), TTT (Phe), ACT (Thr) |
| Leri-Weill dyschondrosteosis | SHOX | CTG (Leu), CGC (Arg), GAG (Glu), GCG (Ala), CTC (Leu), CAC (His), TCC (Ser), AGC (Ser), CGG (Arg), GCC (Ala) |
| Marfan syndrome | FBN1 | GAT (Asp), TGT (Cys), GGA (Gly), GAA (Glu), AGT (Ser), ACA (Thr), ACC (Thr), TTT (Phe), CCA (Pro), AAT (Asn) |
| Mental retardation and distinctive facial features with or without cardiac defects (MRFACD) | MED13L | GAT (Asp), AGT (Ser), TCA (Ser), CCA (Pro), TTT (Phe), ACA (Thr), CCC (Pro), CAT (His), CCT (Pro), CTA (Leu) |
| Mental retardation, autosomal dominant 1 | MBD5 | AGT (Ser), TCA (Ser), CCA (Pro), CTA (Leu), CAT (His), ACA (Thr), CCT (Pro), TTA (Leu), GGA (Gly), CAA (Gln) |

TABLE 5-continued

| Disorder | Gene | Codons |
|---|---|---|
| Mental retardation, autosomal dominant 19 | CTNNB1 | GAT (Asp), GGT (Gly), CAT (His), ACA (Thr), CTT (Leu), CAA (Gln), CTG (Leu), CTA (Leu), GAA (Glu), TCT (Ser) |
| Mental retardation, autosomal dominant 29 | SETBP1 | AGT (Ser), CCA (Pro), CCC (Pro), TCC (Ser), AGC (Ser), TCA (Ser), ACC (Thr), GAG (Glu), CTG (Leu), AGG (Arg) |
| Nail-patella syndrome (NPS) | LMX1B | TCC (Ser), CTG (Leu), GAG (Glu), CCC (Pro), AGC (Ser), CGG (Arg), CAG (Gln), CGC (Arg), CTC (Leu), GAC (Asp) |
| Phelan-McDermid syndrome | SHANK3 | CGC (Arg), CCC (Pro), CTG (Leu), CCG (Pro), GAG (Glu), AGC (Ser), TCC (Ser), CGG (Arg), CTC (Leu), GGC (Gly) |
| Pitt-Hopkins syndrome | TCF4 | TCA (Ser), CAT (His), AGT (Ser), TCC (Ser), CCA (Pro), AGC (Ser), TCT (Ser), GGA (Gly), GAT (Asp), CCT (Pro) |
| Primary pulmonary hypertension 1 | BMPR2 | ACA (Thr), TCA (Ser), GAT (Asp), CAT (His), AGT (Ser), GAA (Glu), CCA (Pro), CTA (Leu), ATA (Ile), ACT (Thr) |
| Rett syndrome (congenital variant) | FOXG1 | CCG (Pro), CCC (Pro), CAC (His), TCC (Ser), CTG (Leu), TCG (Ser), GGC (Gly), CGC (Arg), AGC (Ser), ACC (Thr) |
| Smith-Magenis syndrome (RAI1-associated) | RAI1 | CCC (Pro), TCC (Ser), AGC (Ser), CTG (Leu), ACC (Thr), GAG (Glu), CTC (Leu), CCG (Pro), CGG (Arg), CCA (Pro) |
| Sotos syndrome 1 | NSD1 | TCA (Ser), GAT (Asp), AGT (Ser), CCA (Pro), TTT (Phe), CTA (Leu), GAA (Glu), TCT (Ser), CAT (His), GAG (Glu) |
| Sotos syndrome 2 | NFIX | TCC (Ser), CTG (Leu), TCA (Ser), CCC (Pro), CGG (Arg), CCG (Pro), ACC (Thr), CGC (Arg), GAT (Asp), TTT (Phe) |
| Stickler syndrome type I | COL2A1 | GGT (Gly), CCT (Pro), GGA (Gly), CCC (Pro), GGC (Gly), GAT (Asp), CCA (Pro), GAG (Glu), GAA (Glu), AGA (Arg) |
| Supravalvular aortic stenosis | ELN | GGA (Gly), GGT (Gly), GCA (Ala), CCA (Pro), GGG (Gly), CCT (Pro), GTT (Val), CCC (Pro), GTC (Val), GGC (Gly) |
| SYNGAP1-related intellectual disability | SYNGAP1 | CTG (Leu), GAG (Glu), CGG (Arg), CCC (Pro), TCC (Ser), AGC (Ser), AGT (Ser), CCA (Pro), GGT (Gly), TCA (Ser) |
| Treacher Collins syndrome | TCOF1 | TCA (Ser), GAG (Glu), AGT (Ser), ACC (Thr), AGC (Ser), GGG (Gly), CCA (Pro), GCA (Ala), CCC (Pro), TCC (Ser) |
| Trichorhinophalangeal syndrome type I | TRPS1 | AGT (Ser), TCA (Ser), CAT (His), GAT (Asp), CAA (Gln), ACA (Thr), CTA (Leu), CCA (Pro), GGA (Gly), TCC (Ser) |
| Ulnar-mammary syndrome | TBX3 | TCC (Ser), GCG (Ala), CCG (Pro), CCC (Pro), CTG (Leu), AGC (Ser), ACC (Thr), GCC (Ala), CTC (Leu), TCG (Ser) |
| van der Woude syndrome 1 | IRF6 | CCC (Pro), CTG (Leu), GAT (Asp), CCA (Pro), GAG (Glu), TTT (Phe), ACC (Thr), TGG (Trp), AGC (Ser), CAG (Gln) |
| Waardenburg syndrome type 1 | PAX3 | AGC (Ser), ACC (Thr), CCC (Pro), CTG (Leu), GAG (Glu), AGT (Ser), CCG (Pro), CAA (Gln), CGC (Arg), TCC (Ser) |

TABLE 5-continued

| Disorder | Gene | Codons |
|---|---|---|
| Waardenburg syndrome type 2A | MITF | TCC (Ser), CAT (His), CAA (Gln), CCC (Pro), AGT (Ser), AGC (Ser), GAT (Asp), ACC (Thr), GAA (Glu), GAG (Glu) |
| Waardenburg syndrome type 4C | SOX10 | CCC (Pro), GAG (Glu), TCA (Ser), CAC (His), AGC (Ser), TCC (Ser), GGC (Gly), CTG (Leu), TCG (Ser), CGC (Arg) |

Additionally, the least optimal and most overrepresented codons in the indicated genes were calculated as described above except using a modified tAI value based on a direct quantification of tRNA levels in HEK293 cells (as given in Zheng et al. (2015) Nat. Methods 12 (9): 835-837) rather than estimates of tRNA levels based on tRNA gene copy number.

The three least optimal and most overrepresented codons in the indicated genes are shown in TABLE 6, and the ten least optimal and most overrepresented codons in the indicated genes are shown in TABLE 7.

TABLE 6

| Disorder | Gene | Codons |
|---|---|---|
| 5q-syndrome | RPS14 | CTC (Leu), CCT (Pro), CGC (Arg) |
| Adams-Oliver syndrome 1 | ARHGAP31 | CCC (Pro), CCT (Pro), CTC (Leu) |
| Adams-Oliver syndrome 3 | RBPJ | CTT (Leu), CCT (Pro), TAT (Tyr) |
| Adams-Oliver syndrome 5 | NOTCH1 | CCC (Pro), TGC (Cys), CTC (Leu) |
| Adams-Oliver syndrome 6 | DLL4 | CCC (Pro), TGT (Cys), TGC (Cys) |
| Alagille syndrome 1 | JAG1 | TGT (Cys), CCC (Pro), TGC (Cys) |
| Autoimmune lymphoproliferative syndrome type IA | FAS | AGA (Arg), CTT (Leu), GAA (Glu) |
| Autoimmune lymphoproliferative syndrome type V | CTLA4 | CTC (Leu), CTT (Leu), TAT (Tyr) |
| Autosomal dominant deafness-2A | KCNQ4 | CTC (Leu), CCC (Pro), CGC (Arg) |
| Brain malformations with or without urinary tract defects (BRMUTD) | NFIA | CCC (Pro), CTC (Leu), CCA (Pro) |
| Carney complex type 1 | PRKAR1A | AGA (Arg), CTC (Leu), CTT (Leu) |
| CHARGE syndrome | CHD7 | CCT (Pro), AGA (Arg), CTC (Leu) |
| Cleidocranial dysplasia | RUNX2 | CCC (Pro), CTC (Leu), CCT (Pro) |
| Currarino syndrome | MNX1 | CCC (Pro), GCG (Ala), CTC (Leu) |
| Denys-Drash syndrome / Frasier syndrome | WT1 | CCC (Pro), AGA (Arg), CCG (Pro) |
| Developmental delay, intellectual disability, obesity, and dysmorphic features (DIDOD) | PHIP | AGA (Arg), ATA (Ile), CTT (Leu) |
| DiGeorge syndrome (TBX1-associated) | TBX1 | CCC (Pro), CCG (Pro), GCC (Ala) |
| Dravet syndrome | SCN1A | ATA (Ile), AGA (Arg), CTT (Leu) |
| Duane-radial ray syndrome | SALL4 | CCC (Pro), CTC (Leu), CCT (Pro) |
| Ehlers-Danlos syndrome (classic-like) | TNXB | CCC (Pro), CTC (Leu), CCT (Pro) |
| Ehlers-Danlos syndrome (vascular type) | COL3A1 | CCT (Pro), GGA (Gly), CCC (Pro) |
| Feingold syndrome 1 | MYCN | CCC (Pro), CTC (Leu), GAG (Glu) |
| Frontotemporal lobar degeneration with TDP43 inclusions (FTLD-TDP), GRN-related | GRN | TGC (Cys), CCC (Pro), TGT (Cys) |

TABLE 6-continued

| Disorder | Gene | Codons |
|---|---|---|
| GLUT1 deficiency syndrome | SLC2A1 | CTC (Leu), CCC (Pro), ATC (Ile) |
| Greig cephalopolysyndactyly syndrome | GLI3 | CCC (Pro), CTC (Leu), TCC (Ser) |
| Hereditary hemorrhagic telangiectasia type 1 | ENG | CTC (Leu), CCC (Pro), TCC (Ser) |
| Holoprosencephaly 3 | SHH | CTC (Leu), CCC (Pro), GCG (Ala) |
| Holoprosencephaly 4 | TGIF1 | CTC (Leu), CCC (Pro), TCC (Ser) |
| Holoprosencephaly 5 | ZIC2 | CCC (Pro), GCG (Ala), CTC (Leu) |
| Holt-Oram syndrome | TBX5 | CCC (Pro), CCT (Pro), CTC (Leu) |
| Hypoparathyroidism, sensorineural deafness, and renal disease (HDR) | GATA3 | CCC (Pro), CTC (Leu), TCC (Ser) |
| Kleefstra syndrome 1 | EHMT1 | CCC (Pro), CTC (Leu), GAG (Glu) |
| Klippel-Trenaunay syndrome (AAGF-related) | AGGF1 | AGA (Arg), GAA (Glu), TAT (Tyr) |
| Leri-Weill dyschondrosteosis | SHOX | CTC (Leu), CCC (Pro), GAG (Glu) |
| Marfan syndrome | FBN1 | TGT (Cys), TGC (Cys), CCC (Pro) |
| Mental retardation and distinctive facial features with or without cardiac defects (MRFACD) | MED13L | CTC (Leu), CCC (Pro), CCT (Pro) |
| Mental retardation, autosomal dominant 1 | MBD5 | CCT (Pro), AGA (Arg), CCC (Pro) |
| Mental retardation, autosomal dominant 19 | CTNNB1 | CTT (Leu), CTC (Leu), TAT (Tyr) |
| Mental retardation, autosomal dominant 29 | SETBP1 | CCC (Pro), CTC (Leu), CCT (Pro) |
| Nail-patella syndrome (NPS) | LMX1B | CCC (Pro), CTC (Leu), TCC (Ser) |
| Phelan-McDermid syndrome | SHANK3 | CCC (Pro), CTC (Leu), CGC (Arg) |
| Pitt-Hopkins syndrome | TCF4 | CCT (Pro), CTC (Leu), AGA (Arg) |
| Primary pulmonary hypertension 1 | BMPR2 | AGA (Arg), CTT (Leu), ATA (Ile) |
| Rett syndrome (congenital variant) | FOXG1 | CCC (Pro), CTC (Leu), CCG (Pro) |
| Smith-Magenis syndrome (RAI1-associated) | RAI1 | CCC (Pro), CTC (Leu), TCC (Ser) |
| Sotos syndrome 1 | NSD1 | CCT (Pro), AGA (Arg), CCC (Pro) |
| Sotos syndrome 2 | NFIX | CCC (Pro), TCC (Ser), CCT (Pro) |
| Stickler syndrome type I | COL2A1 | CCT (Pro), CCC (Pro), GGA (Gly) |
| Supravalvular aortic stenosis | ELN | GGA (Gly), CCT (Pro), CCC (Pro) |
| SYNGAP1-related intellectual disability | SYNGAP1 | CCC (Pro), CTC (Leu), GAG (Glu) |
| Treacher Collins syndrome | TCOF1 | CCC (Pro), CCT (Pro), GAG (Glu) |
| Trichorhinophalangeal syndrome type I | TRPS1 | AGA (Arg), CCT (Pro), CCC (Pro) |
| Ulnar-mammary syndrome | TBX3 | CCC (Pro), CTC (Leu), TCC (Ser) |
| van der Woude syndrome 1 | IRF6 | CCC (Pro), CTC (Leu), CCT (Pro) |

TABLE 6-continued

| Disorder | Gene | Codons |
|---|---|---|
| Waardenburg syndrome type 1 | PAX3 | CCC (Pro), CTC (Leu), CCT (Pro) |
| Waardenburg syndrome type 2A | MITF | CCC (Pro), CTC (Leu), CTT (Leu) |
| Waardenburg syndrome type 4C | SOX10 | CCC (Pro), CTC (Leu), GAG (Glu) |

TABLE 7

| Disorder | Gene | Codons |
|---|---|---|
| 5q-syndrome | RPS14 | CTC (Leu), CCT (Pro), CGC (Arg), CCC (Pro), ATC (Ile), GGA (Gly), CTT (Leu), GAA (Glu), AAG (Lys), GCC (Ala) |
| Adams-Oliver syndrome 1 | ARHGAP31 | CCC (Pro), CCT (Pro), CTC (Leu), GAG (Glu), AGA (Arg), CTT (Leu), CCA (Pro), TCC (Ser), GAA (Glu), GCA (Ala) |
| Adams-Oliver syndrome 3 | RBPJ | CTT (Leu), CCT (Pro), TAT (Tyr), ATA (Ile), AGA (Arg), GCA (Ala), CTC (Leu), GAA (Glu), ACA (Thr), GGA (Gly) |
| Adams-Oliver syndrome 5 | NOTCH1 | CCC (Pro), TGC (Cys), CTC (Leu), GAG (Glu), TGT (Cys), TCC (Ser), TAC (Tyr), CGC (Arg), AAC (Asn), GCC (Ala) |
| Adams-Oliver syndrome 6 | DLL4 | CCC (Pro), TGT (Cys), TGC (Cys), CTC (Leu), CGC (Arg), TCC (Ser), CCT (Pro), TAC (Tyr), TAT (Tyr), GAG (Glu) |
| Alagille syndrome 1 | JAG1 | TGT (Cys), CCC (Pro), TGC (Cys), CTC (Leu), CCT (Pro), AGA (Arg), TAT (Tyr), AAC (Asn), AAT (Asn), TCC (Ser) |
| Autoimmune lymphoproliferative syndrome type IA | FAS | AGA (Arg), CTT (Leu), GAA (Glu), TGT (Cys), CTC (Leu), AAT (Asn), TGC (Cys), ATA (Ile), CCT (Pro), TTG (Leu) |
| Autoimmune lymphoproliferative syndrome type V | CTLA4 | CTC (Leu), CTT (Leu), TAT (Tyr), CCC (Pro), CCT (Pro), TTT (Phe), CCA (Pro), GCA (Ala), TAC (Tyr), TGC (Cys) |
| Autosomal dominant deafness-2A | KCNQ4 | CTC (Leu), CCC (Pro), CGC (Arg), TCC (Ser), TAC (Tyr), ATC (Ile), GAG (Glu), GCC (Ala), CTG (Leu), CCT (Pro) |
| Brain malformations with or without urinary tract defects (BRMUTD) | NFIA | CCC (Pro), CTC (Leu), CCA (Pro), CCT (Pro), CTT (Leu), GCA (Ala), AGA (Arg), TCC (Ser), ACA (Thr), AGT (Ser) |
| Carney complex type 1 | PRKAR1A | AGA (Arg), CTC (Leu), CTT (Leu), TAT (Tyr), GCA (Ala), GAA (Glu), GAG (Glu), CCT (Pro), TTT (Phe), CCC (Pro) |
| CHARGE syndrome | CHD7 | CCT (Pro), AGA (Arg), CTC (Leu), CCC (Pro), GAA (Glu), CTT (Leu), ATA (Ile), GAG (Glu), GCA (Ala), CCA (Pro) |
| Cleidocranial dysplasia | RUNX2 | CCC (Pro), CTC (Leu), CCT (Pro), TCC (Ser), GCG (Ala), CCG (Pro), AGA (Arg), CGC (Arg), ACC (Thr), GCA (Ala) |
| Currarino syndrome | MNX1 | CCC (Pro), GCG (Ala), CTC (Leu), CCG (Pro), CGC (Arg), GCC (Ala), GAG (Glu), TCC (Ser), GGC (Gly), CTG (Leu) |
| Denys-Drash syndrome/ Frasier syndrome | WT1 | CCC (Pro), AGA (Arg), CCG (Pro), TAC (Tyr), TGT (Cys), CTC (Leu), GCG (Ala), TCC (Ser), CCT (Pro), AGC (Ser) |
| Developmental delay, intellectual disability, obesity, and dysmorphic features (DIDOD) | PHIP | AGA (Arg), ATA (Ile), CTT (Leu), CCT (Pro), GAA (Glu), TAT (Tyr), CTA (Leu), GCA (Ala), CCC (Pro), GGA (Gly) |

TABLE 7-continued

| Disorder | Gene | Codons |
|---|---|---|
| DiGeorge syndrome (TBX1-associated) | TBX1 | CCC (Pro), CCG (Pro), GCC (Ala), CTC (Leu), GCG (Ala), TAC (Tyr), CGC (Arg), TAT (Tyr), GAG (Glu), TTC (Phe) |
| Dravet syndrome | SCN1A | ATA (Ile), AGA (Arg), CTT (Leu), CTC (Leu), TAT (Tyr), GAA (Glu), CTA (Leu), TTT (Phe), AAT (Asn), CCT (Pro) |
| Duane-radial ray syndrome | SALL4 | CCC (Pro), CTC (Leu), CCT (Pro), TCC (Ser), GAG (Glu), ACC (Thr), TGT (Cys), ATC (Ile), CTT (Leu), AGC (Ser) |
| Ehlers-Danlos syndrome (classic-like) | TNXB | CCC (Pro), CTC (Leu), CCT (Pro), GAG (Glu), CGC (Arg), TCC (Ser), TAC (Tyr), ACC (Thr), GGG (Gly), ACA (Thr) |
| Ehlers-Danlos syndrome (vascular type) | COL3A1 | CCT (Pro), GGA (Gly), CCC (Pro), GGT (Gly), CCA (Pro), AGA (Arg), GAA (Glu), CTT (Leu), CTC (Leu), GCA (Ala) |
| Feingold syndrome 1 | MYCN | CCC (Pro), CTC (Leu), GAG (Glu), TCC (Ser), CCG (Pro), CGC (Arg), GCC (Ala), GCG (Ala), CTT (Leu), AAG (Lys) |
| Frontotemporal lobar degeneration with TDP43 inclusions (FTLD-TDP), GRN-related | GRN | TGC (Cys), CCC (Pro), TGT (Cys), CCT (Pro), CTC (Leu), TCC (Ser), AGA (Arg), GCC (Ala), ACC (Thr), CGC (Arg) |
| GLUT1 deficiency syndrome | SLC2A1 | CTC (Leu), CCC (Pro), ATC (Ile), TCC (Ser), TTC (Phe), CTG (Leu), GAG (Glu), CGC (Arg), TAT (Tyr), GCC (Ala) |
| Greig cephalopolysyndactyly syndrome | GLI3 | CCC (Pro), CTC (Leu), TCC (Ser), CCT (Pro), AGA (Arg), AGC (Ser), CTT (Leu), CCA (Pro), GAG (Glu), CCG (Pro) |
| Hereditary hemorrhagic telangiectasia type 1 | ENG | CTC (Leu), CCC (Pro), TCC (Ser), AGC (Ser), CTT (Leu), GAG (Glu), ATC (Ile), ACC (Thr), CTG (Leu), GCC (Ala) |
| Holoprosencephaly 3 | SHH | CTC (Leu), CCC (Pro), GCG (Ala), CGC (Arg), TAC (Tyr), GAG (Glu), CTG (Leu), GCC (Ala), AGA (Arg), TCG (Ser) |
| Holoprosencephaly 4 | TGIF1 | CTC (Leu), CCC (Pro), TCC (Ser), CTT (Leu), CCT (Pro), CTA (Leu), CCA (Pro), TCT (Ser), AGA (Arg), CCG (Pro) |
| Holoprosencephaly 5 | ZIC2 | CCC (Pro), GCG (Ala), CTC (Leu), TCC (Ser), CCG (Pro), CGC (Arg), CAC (His), GAG (Glu), GGC (Gly), TTC (Phe) |
| Holt-Oram syndrome | TBX5 | CCC (Pro), CCT (Pro), CTC (Leu), TCC (Ser), TAC (Tyr), AGA (Arg), CTA (Leu), GAG (Glu), ACC (Thr), CCA (Pro) |
| Hypoparathyroidism, sensorineural deafness, and renal disease (HDR) | GATA3 | CCC (Pro), CTC (Leu), TCC (Ser), CCG (Pro), TAC (Tyr), AGA (Arg), ACC (Thr), CAC (His), TCG (Ser), AGC (Ser) |
| Kleefstra syndrome 1 | EHMT1 | CCC (Pro), CTC (Leu), GAG (Glu), GCA (Ala), TGC (Cys), TCC (Ser), GCC (Ala), AGA (Arg), CTT (Leu), CCT (Pro) |
| Klippel-Trenaunay syndrome (AAGF-related) | AGGF1 | AGA (Arg), GAA (Glu), TAT (Tyr), CCT (Pro), CTT (Leu), CTC (Leu), GAT (Asp), AAT (Asn), GAG (Glu), GCA (Ala) |
| Leri-Weill dyschondrosteosis | SHOX | CTC (Leu), CCC (Pro), GAG (Glu), CGC (Arg), GCG (Ala), TCC (Ser), GCC (Ala), AGA (Arg), CTG (Leu), CCG (Pro) |

TABLE 7-continued

| Disorder | Gene | Codons |
|---|---|---|
| Marfan syndrome | FBN1 | TGT (Cys), TGC (Cys), CCC (Pro), CCT (Pro), AGA (Arg), GGA (Gly), CTC (Leu), GAA (Glu), AAT (Asn), TAT (Tyr) |
| Mental retardation and distinctive facial features with or without cardiac defects (MRFACD) | MED13L | CTC (Leu), CCC (Pro), CCT (Pro), CTT (Leu), AGA (Arg), CCA (Pro), ATA (Ile), GCA (Ala), TAT (Tyr), TCC (Ser) |
| Mental retardation, autosomal dominant 1 | MBD5 | CCT (Pro), AGA (Arg), CCC (Pro), CTC (Leu), CTT (Leu), CCA (Pro), CTA (Leu), ATA (Ile), AAT (Asn), GCA (Ala) |
| Mental retardation, autosomal dominant 19 | CTNNB1 | CTT (Leu), CTC (Leu), TAT (Tyr), CCT (Pro), AGA (Arg), GAA (Glu), GCA (Ala), ATA (Ile), GGA (Gly), TCT (Ser) |
| Mental retardation, autosomal dominant 29 | SETBP1 | CCC (Pro), CTC (Leu), CCT (Pro), CCA (Pro), TCC (Ser), AGA (Arg), CTT (Leu), GCA (Ala), AAG (Lys), GAG (Glu) |
| Nail-patella syndrome (NPS) | LMX1B | CCC (Pro), CTC (Leu), TCC (Ser), TGC (Cys), GAG (Glu), TAC (Tyr), CGC (Arg), AAG (Lys), AGA (Arg), CCG (Pro) |
| Phelan-McDermid syndrome | SHANK3 | CCC (Pro), CTC (Leu), CGC (Arg), CCG (Pro), GAG (Glu), TCC (Ser), CCT (Pro), GCC (Ala), CTG (Leu), GCG (Ala) |
| Pitt-Hopkins syndrome | TCF4 | CCT (Pro), CTC (Leu), AGA (Arg), CCC (Pro), TCC (Ser), TAT (Tyr), CTT (Leu), CCA (Pro), TCT (Ser), GGA (Gly) |
| Primary pulmonary hypertension 1 | BMPR2 | AGA (Arg), CTT (Leu), ATA (Ile), CCC (Pro), CCT (Pro), TAT (Tyr), CTC (Leu), GCA (Ala), GAA (Glu), AAT (Asn) |
| Rett syndrome (congenital variant) | FOXG1 | CCC (Pro), CTC (Leu), CCG (Pro), TCC (Ser), TAC (Tyr), CGC (Arg), GCC (Ala), GAG (Glu), GCG (Ala), CAC (His) |
| Smith-Magenis syndrome (RAI1-associated) | RAI1 | CCC (Pro), CTC (Leu), TCC (Ser), CCT (Pro), GAG (Glu), GCC (Ala), CCG (Pro), AAG (Lys), CCA (Pro), ACC (Thr) |
| Sotos syndrome 1 | NSD1 | CCT (Pro), AGA (Arg), CCC (Pro), CTT (Leu), CTC (Leu), TGT (Cys), ATA (Ile), GAA (Glu), CCA (Pro), TCT (Ser) |
| Sotos syndrome 2 | NFIX | CCC (Pro), TCC (Ser), CCT (Pro), CTC (Leu), CCG (Pro), ATC (Ile), CGC (Arg), TAC (Tyr), AGA (Arg), GCA (Ala) |
| Stickler syndrome type I | COL2A1 | CCT (Pro), CCC (Pro), GGA (Gly), GGT (Gly), AGA (Arg), CTC (Leu), GAA (Glu), GGC (Gly), GAG (Glu), CCA (Pro) |
| Supravalvular aortic stenosis | ELN | GGA (Gly), CCT (Pro), CCC (Pro), GCA (Ala), CTC (Leu), CTT (Leu), CCA (Pro), GGT (Gly), GCT (Ala), GGG (Gly) |
| SYNGAP1-related intellectual disability | SYNGAP1 | CCC (Pro), CTC (Leu), GAG (Glu), TCC (Ser), CCT (Pro), CCA (Pro), TAT (Tyr), CTG (Leu), CGC (Arg), CTA (Leu) |
| Treacher Collins syndrome | TCOF1 | CCC (Pro), CCT (Pro), GAG (Glu), GCA (Ala), AGA (Arg), GCC (Ala), TCC (Ser), CCA (Pro), AAG (Lys), GGG (Gly) |
| Trichorhinophalangeal syndrome type I | TRPS1 | AGA (Arg), CCT (Pro), CCC (Pro), TAT (Tyr), CTC (Leu), CTT (Leu), AAT (Asn), TGT (Cys), GAA (Glu), GCA (Ala) |
| Ulnar-mammary syndrome | TBX3 | CCC (Pro), CTC (Leu), TCC (Ser), GCG (Ala), GCC (Ala), CCG (Pro), AGA (Arg), CCT (Pro), GAG (Glu), CGC (Arg) |

TABLE 7-continued

| Disorder | Gene | Codons |
|---|---|---|
| van der Woude syndrome 1 | IRF6 | CCC (Pro), CTC (Leu), CCT (Pro), AGA (Arg), GAG (Glu), CCA (Pro), ATC (Ile), GAA (Glu), TAT (Tyr), TAC (Tyr) |
| Waardenburg syndrome type 1 | PAX3 | CCC (Pro), CTC (Leu), CCT (Pro), AGA (Arg), GAG (Glu), TAC (Tyr), TCC (Ser), TAT (Tyr), ACC (Thr), AGC (Ser) |
| Waardenburg syndrome type 2A | MITF | CCC (Pro), CTC (Leu), CTT (Leu), AGA (Arg), ATA (Ile), TCC (Ser), GAA (Glu), GAG (Glu), TAT (Tyr), GCA (Ala) |
| Waardenburg syndrome type 4C | SOX10 | CCC (Pro), CTC (Leu), GAG (Glu), TCC (Ser), TAC (Tyr), TAT (Tyr), GCC (Ala), CCA (Pro), CGC (Arg), GGG (Gly) |

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. A method of increasing expression in a mammalian cell of a gene product encoded by a gene containing a first, second, and third non-optimal codon, the method comprising introducing into the cell an effective amount of a first, second, and third exogenous transfer RNA (tRNA) that each (i) comprises an anticodon that hybridizes to the first, second, and third non-optimal codon, respectively, and (ii) is capable of being aminoacylated with an amino acid, wherein introduction of the first, second, and third exogenous tRNAs into the cell increases the expression of the gene product relative to a similar cell lacking the first, second, and third exogenous tRNAs, and wherein the first, second, and/or third non-optimal codon is selected from ATA, GTA, and AGA.

2. The method of claim 1, wherein the cell is a human cell.

3. The method of claim 1, wherein the gene is selected from AGGF1, ARHGAP31, BMPR2, CHD7, COL2A1, COL3A1, CTLA4, CTNNB1, DLL4, EHMT1, ELN, ENG, FAS, FBN1, FOXG1, GATA3, GLI3, GRN, IRF6, JAG1, KCNQ4, LMX1B, MBD5, MED13L, MITF, MNX1, MYCN, NFIA, NFIX, NOTCH1, NSD1, PAX3, PHIP, PRKAR1A, RAI1, RBPJ, RPS14, RUNX2, SALL4, SCN1A, SETBP1, SHANK3, SHH, SHOX, SLC2A1/GLUT1, SOX10, SYNGAP1, TBX1, TBX3, TBX5, TCF4, TCOF1, TGIF1, TNXB, TRPS1, WT1, and ZIC2.

4. The method of claim 1, wherein the gene is SCN1A.

5. The method of claim 1, wherein the first, second, and/or third tRNA is selected from a tRNA comprising the nucleotide sequence of SEQ ID NO: 1, SEQ ID NO: 2 and SEQ ID NO: 3.

6. A method of increasing expression in a mammalian cell of a gene product encoded by a gene containing a first, second, and third non-optimal codon, comprising introducing into the cell an effective amount of a combination of three expression vectors, wherein upon administration to the mammalian cell, each expression vector is capable of expressing an exogenous tRNA that (i) comprises an anti-codon that hybridizes to the first, second, or third non-optimal codon, respectively, and (ii) is capable of being aminoacylated with an amino acid, wherein expression of the first, second, and third exogenous tRNAs in the cell increases the expression of the gene product relative to a similar cell lacking the first, second, and third exogenous tRNAs, and wherein the first, second, and/or third non-optimal codon is selected from ATA, GTA, and AGA.

7. The method of claim 6, wherein the first, second, and/or third expression vectors are the same.

8. The method of claim 6, wherein the first, second, and/or third expression vector is a viral vector.

9. The method of claim 8, wherein the first, second, and/or third expression vector is an adeno-associated virus (AAV) vector.

10. The method of claim 6, wherein the first, second, and/or third expression vector comprises a nucleotide sequence selected from SEQ ID NO: 4, SEQ ID NO: 5, SEQ ID NO: 6, SEQ ID NO: 7, SEQ ID NO: 8, and SEQ ID NO: 9.

* * * * *

SEQUENCE LISTING

<160> NUMBER OF SEQ ID NOS: 9

<210> SEQ ID NO 1
<211> LENGTH: 92
<212> TYPE: DNA
<213> ORGANISM: Artificial Sequence
<220> FEATURE:
<223> OTHER INFORMATION: Synthetic Construct

<400> SEQUENCE: 1
gctccagtgg cgcaatcggt tagcgcgcgg tacttataca gcagtacatg cagagcaatg     60
ccgaggttgt gagttcgagc ctcacctgga gc                                   92

<210> SEQ ID NO 2
<211> LENGTH: 73
<212> TYPE: DNA
<213> ORGANISM: Artificial Sequence
<220> FEATURE:
<223> OTHER INFORMATION: Synthetic Construct

<400> SEQUENCE: 2
ggttccatag tgtagtggtt atcacgtctg ctttacacgc agaaggtcct gggttcgagc     60
cccagtggaa cca                                                        73

<210> SEQ ID NO 3
<211> LENGTH: 85
<212> TYPE: DNA
<213> ORGANISM: Artificial Sequence

```
<220> FEATURE:
<223> OTHER INFORMATION: Synthetic Construct

<400> SEQUENCE: 3
ggctccgtgg cgcaatggat agcgcattgg acttctagag gctgaaggca ttcaaaggtt    60
ccgggttcga gtcccggcgg agtcg                                          85

<210> SEQ ID NO 4
<211> LENGTH: 493
<212> TYPE: DNA
<213> ORGANISM: Artificial Sequence
<220> FEATURE:
<223> OTHER INFORMATION: Synthetic Construct

<400> SEQUENCE: 4
aggctaggcg gcccctccat ccccgagggc gacactcgca ggcttccccg gctcgatcgg    60
ctgcggaaca gccgggagct cggcgcgaag tcgcagaagg ctcgggcctg ggctcgcgcc   120
gcgaacgcgc atgctctgcc gaggcccgcc gcgggcgcca gcgcaccctg atagagccat   180
cacgaggccc attcagcaga gctccagtgg cgcaatcggt tagcgcgcgg tacttataca   240
gcagtacatg cagagcaatg ccgaggttgt gagttcgagc ctcacctgga gcaagaccct   300
tttggatgtt cgcaaccccc tttgtgtatc tcgttgccag aagtaaggag tctctcttta   360
gtcttctccc ttcttgtttc taactgctct gccgcacgtc cccattggcc gcaagcagga   420
agcagctcgc agtggactct caatacccct tttccgagct acttgttgcc accgcgcgac   480
atccagccgc tcg                                                     493

<210> SEQ ID NO 5
<211> LENGTH: 473
<212> TYPE: DNA
<213> ORGANISM: Artificial Sequence
<220> FEATURE:
<223> OTHER INFORMATION: Synthetic Construct

<400> SEQUENCE: 5
ggcctcgccc tggtcccagg ggccgcgact gtggcgggca gggaagacaa gccgcccaaa    60
cgccggagcc cgagactcga agccgccgca aactcctcgc ctcggggggcg gggtcacggt   120 ggagaggcgg ggctccggcg gagggaccgg aactgctgtg agtctatgaa taaagtccca   180
acaatattct tcctcgtaga ggttccatag tgtagtggtt atcacgtctg ctttacacgc   240
agaaggtcct gggttcgagc cccagtggaa ccatagccgt aaggcggctg ttttttgcttt   300 tatagggttt cgttgtttgg gttaaaaaaa aaaagggtt tgggtaaac aaacaaaaaa    360 aaccaaaaag cgacaacgaa gtgttttttct ttgtcctttt tttcttttta attttttggc   420 atgttttttct cgcagaagtg aaatgacaga taccctctcc tatcccacaa ggt        473

<210> SEQ ID NO 6
<211> LENGTH: 485
<212> TYPE: DNA
<213> ORGANISM: Artificial Sequence
<220> FEATURE:
<223> OTHER INFORMATION: Synthetic Construct

<400> SEQUENCE: 6
ctcaactggg tcgccgacct tgttgagggg cgaccactgc ggggagaccg agagcctgcg    60
gctggcgttt gaggcggatg gcagtgccct gagcgcggcg gctgggtctc ggtgacactg   120
acgacgggag gcgcggtcgg aagagcgcgg ggccgtcgcc tctggcttaa catagcagat   180
```

```
gcgctgagac tccaacaggt ggctccgtgg cgcaatggat agcgcattgg acttctagag      240
gctgaaggca ttcaaaggtt ccgggttcga gtcccggcgg agtcgtaacg ctttttccc       300 tccccctac aatttatttt ctgcctccat catgtctctt attttttttt tttgctaaac       360
ggtttaactt ctctctcatt ccctgctctc gcagttcact gcattcggtt cttgcggtcc      420
tttcttaagc ggctcgcagg gtcccgagcc cctcagctcc ccgggcctcg gtggcccagg      480
gccca                                                                  485

<210> SEQ ID NO 7
<211> LENGTH: 185
<212> TYPE: DNA
<213> ORGANISM: Artificial Sequence
<220> FEATURE:
<223> OTHER INFORMATION: Synthetic Construct

<400> SEQUENCE: 7
gcgccagcgc accctgatag agccatcacg aggcccattc agcagagctc cagtggcgca       60
atcggttagc gcgcggtact tatacagcag tacatgcaga gcaatgccga ggttgtgagt      120
tcgagcctca cctggagcaa gaccctttttg gatgttcgca acccctttttg tgtatctcgt    180 tgcca                                                                  185

<210> SEQ ID NO 8
<211> LENGTH: 165
<212> TYPE: DNA
<213> ORGANISM: Artificial Sequence
<220> FEATURE:
<223> OTHER INFORMATION: Synthetic Construct

<400> SEQUENCE: 8
gctgtgagtc tatgaataaa gtcccaacaa tattcttcct cgtagaggtt ccatagtgta       60
gtggttatca cgtctgcttt acacgcagaa ggtcctgggt tcgagcccca gtggaaccat      120
agccgtaagg cggctgtttt tgcttttata gggtttcgtt gtttg                      165

<210> SEQ ID NO 9
<211> LENGTH: 177
<212> TYPE: DNA
<213> ORGANISM: Artificial Sequence
<220> FEATURE:
<223> OTHER INFORMATION: Synthetic Construct

<400> SEQUENCE: 9
gtcgcctctg gcttaacata gcagatgcgc tgagactcca acaggtggct ccgtggcgca       60
atggatagcg cattggactt ctagaggctg aaggcattca aaggttccgg gttcgagtcc      120
cggcggagtc gtaacgcttt tttccctccc ccctacaatt tatttctgc ctccatc          177
```